(12) United States Patent
Steinke et al.

(10) Patent No.: US 12,377,274 B2
(45) Date of Patent: Aug. 5, 2025

(54) INTERPOLATION METHODS FOR NEURAL RESPONSES

(71) Applicant: Boston Scientific Neuromodulation Corporation, Valencia, CA (US)

(72) Inventors: G. Karl Steinke, Valencia, CA (US); Joseph Costello, Ann Arbor, MI (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 420 days.

(21) Appl. No.: 17/812,660

(22) Filed: Jul. 14, 2022

(65) Prior Publication Data

US 2023/0023842 A1 Jan. 26, 2023

Related U.S. Application Data

(60) Provisional application No. 63/224,751, filed on Jul. 22, 2021.

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01)

(58) Field of Classification Search
None
See application file for complete search history.

(56) References Cited

U.S. PATENT DOCUMENTS 5,311,873 A * 5/1994 Savard ............... A61N 1/372
128/898
6,052,624 A 4/2000 Mann
(Continued)

FOREIGN PATENT DOCUMENTS

AU 2014351064 7/2019
AU 2019216650 A1 9/2019
(Continued)

OTHER PUBLICATIONS

Qian, Xing, et al., "A Method for Removal of Deep Brain Stimulation Artifact From Local Field Potentials," IEEE Transactions On Neural Systems and Rehabilitation Engineering, vol. 25, No. 12, Dec. 2017, 10 pages.
(Continued)

*Primary Examiner* — Deborah L Malamud
(74) *Attorney, Agent, or Firm* — Lewis & Reese, PLLC

(57) ABSTRACT

Methods and systems for using evoked neural response to inform aspects of deep brain stimulation therapy are disclosed. According to some embodiments, a series of evoked neural response signals are recorded, and one or more waveform features are extracted from each of the signals. The waveform features can be used as biomarkers and or control signals for informing aspects of the therapy, such as lead implantation/localization, optimization of stimulation parameters, and/or closed loop feedback for maintaining chronic therapy. Embodiments include a check to determine and classify if any of the recorded neural response signals or portions thereof are corrupted. In the event that any of the signals are corrupted, values for the waveform features for the corrupted signals are interpolated using uncorrupted neural response signals in the series and/or uncorrupted portions of the problem neural response signal.

16 Claims, 11 Drawing Sheets

(56) References Cited

U.S. PATENT DOCUMENTS

| | | |
|---|---|---|
| 6,181,969 B1 | 1/2001 | Gord |
| 6,393,325 B1 | 5/2002 | Mann et al. |
| 6,490,486 B1 | 12/2002 | Bradley |
| 6,609,032 B1 | 8/2003 | Woods et al. |
| 6,845,267 B2 | 1/2005 | Harrison et al. |
| 6,909,917 B2 | 6/2005 | Woods et al. |
| 6,950,707 B2 | 9/2005 | Whitehurst |
| 7,555,346 B2 | 6/2009 | Woods et al. |
| 7,582,062 B2 | 9/2009 | Magill et al. |
| 7,831,307 B1 | 11/2010 | Moffitt |
| 7,930,030 B2 | 4/2011 | Woods et al. |
| 8,121,701 B2 | 2/2012 | Woods et al. |
| 8,180,601 B2 | 5/2012 | Butson et al. |
| 8,265,762 B2 | 9/2012 | Woods et al. |
| 8,401,658 B2 | 3/2013 | Woods et al. |
| 8,606,362 B2 | 12/2013 | He et al. |
| 8,620,436 B2 | 12/2013 | Parramon et al. |
| 8,805,524 B2 | 8/2014 | Woods et al. |
| 8,812,124 B2 | 8/2014 | Lee |
| 8,855,773 B2 | 10/2014 | Kokones et al. |
| 8,868,193 B2 | 10/2014 | Ranu et al. |
| 8,868,196 B2 | 10/2014 | Lee et al. |
| 8,868,197 B2 | 10/2014 | Lee |
| 8,909,350 B2 | 12/2014 | Lee |
| 8,914,119 B2 | 12/2014 | Wu et al. |
| 8,958,615 B2 | 2/2015 | Blum et al. |
| 9,014,820 B2 | 4/2015 | Lee et al. |
| 9,050,473 B2 | 6/2015 | Woods et al. |
| 9,072,905 B2 | 7/2015 | Kokones et al. |
| 9,205,261 B2 | 12/2015 | Kim et al. |
| 9,248,280 B2 | 2/2016 | Moffitt et al. |
| 9,381,356 B2 | 7/2016 | Parker et al. |
| 9,387,328 B2 | 7/2016 | Lee |
| 9,387,334 B2 | 7/2016 | Lee et al. |
| 9,411,935 B2 | 8/2016 | Moffitt et al. |
| 9,511,231 B1 | 12/2016 | Kent et al. |
| 10,183,167 B2 | 1/2019 | Steinke et al. |
| 10,183,168 B2 | 1/2019 | Baru et al. |
| 10,195,439 B2 | 2/2019 | Steinke et al. |
| 10,207,113 B2 | 2/2019 | Lee et al. |
| 10,207,114 B2 | 2/2019 | Lee |
| 10,249,041 B2 | 4/2019 | Varkuti |
| 10,252,059 B2 | 4/2019 | Steinke et al. |
| 10,286,205 B2 | 5/2019 | Steinke et al. |
| 10,406,368 B2 | 9/2019 | Hershey et al. |
| 10,463,860 B2 | 11/2019 | Sinclair et al. |
| 10,549,097 B2 | 2/2020 | Zhang et al. |
| 10,576,292 B2 | 3/2020 | Orinski |
| 10,974,051 B2 | 4/2021 | Steinke et al. |
| 10,994,131 B2 | 5/2021 | Durand et al. |
| 11,020,004 B2 | 6/2021 | Varkuti |
| 11,123,563 B2 | 9/2021 | Mustakos et al. |
| 11,195,609 B2 | 12/2021 | Mustakos et al. |
| 11,344,732 B2 | 5/2022 | Moffitt et al. |
| 11,376,433 B2 | 7/2022 | Zhang et al. |
| 11,478,633 B2 | 10/2022 | Tinkhauser et al. |
| 2004/0133248 A1* | 7/2004 | Frei .............. A61N 1/37264 607/45 |
| 2005/0065427 A1 | 3/2005 | Magill et al. |
| 2006/0224222 A1 | 10/2006 | Bradley et al. |
| 2007/0244407 A1 | 10/2007 | Osorio |
| 2009/0118786 A1 | 5/2009 | Meadows et al. |
| 2009/0118787 A1 | 5/2009 | Moffitt et al. |
| 2009/0299421 A1 | 12/2009 | Sawchuk |
| 2010/0305660 A1 | 12/2010 | Hegi et al. |
| 2011/0105939 A1 | 5/2011 | Yong et al. |
| 2012/0046712 A1 | 2/2012 | Woods et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2014/0163639 A1 | 6/2014 | Zhu |
| 2014/0243926 A1 | 8/2014 | Carcieri |
| 2014/0277282 A1 | 9/2014 | Jaax |
| 2014/0296737 A1 | 10/2014 | Parker et al. |
| 2014/0350634 A1* | 11/2014 | Grill .............. A61N 1/36082 607/45 |
| 2014/0378941 A1 | 12/2014 | Su et al. |
| 2015/0039048 A1 | 2/2015 | Woods et al. |
| 2015/0066108 A1 | 3/2015 | Shi et al. |
| 2015/0080982 A1 | 3/2015 | Funderburk |
| 2015/0088228 A1 | 3/2015 | Moffitt |
| 2015/0157861 A1 | 6/2015 | Aghassian |
| 2015/0231402 A1 | 8/2015 | Aghassian |
| 2015/0360033 A1 | 12/2015 | Koubeissi et al. |
| 2015/0360038 A1 | 12/2015 | Zottola et al. |
| 2016/0045747 A1 | 2/2016 | Jiang et al. |
| 2016/0158565 A1 | 6/2016 | Lee |
| 2016/0287126 A1 | 10/2016 | Parker et al. |
| 2016/0339251 A1 | 11/2016 | Kent et al. |
| 2016/0361542 A1 | 12/2016 | Kaula et al. |
| 2017/0120056 A1 | 5/2017 | Woods et al. |
| 2017/0128019 A1* | 5/2017 | Shao ................. A61B 5/0015 |
| 2017/0189687 A1 | 7/2017 | Steinke et al. |
| 2017/0189689 A1 | 7/2017 | Steinke et al. |
| 2017/0281959 A1 | 10/2017 | Serrano Carmona et al. |
| 2017/0333701 A1 | 11/2017 | Bradley et al. |
| 2017/0333715 A1 | 11/2017 | De Ridder et al. |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0110987 A1 | 4/2018 | Parker |
| 2018/0132747 A1 | 5/2018 | Parker et al. |
| 2018/0133459 A1 | 5/2018 | Parker et al. |
| 2018/0140831 A1 | 5/2018 | Feldman et al. |
| 2018/0140843 A1 | 5/2018 | Kent et al. |
| 2018/0221644 A1 | 8/2018 | Grill et al. |
| 2019/0030323 A1 | 1/2019 | Koka et al. |
| 2019/0038902 A1* | 2/2019 | Kaemmerer ....... A61N 1/36139 |
| 2019/0070429 A1 | 3/2019 | Hincapie Ordonez et al. |
| 2019/0076645 A1 | 3/2019 | Bower et al. |
| 2019/0083796 A1 | 3/2019 | Weerakoon et al. |
| 2019/0099602 A1 | 4/2019 | Esteller et al. |
| 2019/0143120 A1* | 5/2019 | Sinclair .......... A61N 1/36167 607/45 |
| 2019/0175915 A1 | 6/2019 | Brill et al. |
| 2019/0209844 A1 | 7/2019 | Esteller et al. |
| 2019/0209851 A1 | 7/2019 | Kothandaraman et al. |
| 2019/0232062 A1 | 8/2019 | Falowski |
| 2019/0262609 A1 | 8/2019 | Brill et al. |
| 2019/0274637 A1 | 9/2019 | Wilson et al. |
| 2019/0275331 A1 | 9/2019 | Zhu |
| 2019/0299006 A1 | 10/2019 | Marnfeldt |
| 2019/0365271 A1* | 12/2019 | Ghosh .............. A61B 5/282 |
| 2019/0366094 A1 | 12/2019 | Esteller et al. |
| 2019/0381318 A1 | 12/2019 | Sinclair et al. |
| 2020/0001086 A1 | 1/2020 | Fernandez et al. |
| 2020/0001091 A1 | 1/2020 | Marnfeldt |
| 2020/0038660 A1 | 2/2020 | Torgerson |
| 2020/0138324 A1 | 5/2020 | Sinclair et al. |
| 2020/0147393 A1 | 5/2020 | Zhang et al. |
| 2020/0305744 A1 | 10/2020 | Weerakoon et al. |
| 2020/0305745 A1 | 10/2020 | Wagenbach et al. |
| 2020/0335221 A1 | 10/2020 | Fichtinger et al. |
| 2020/0391037 A1 | 12/2020 | Grado et al. |
| 2021/0016091 A1 | 1/2021 | Parker et al. |
| 2021/0046322 A1 | 2/2021 | Zhang et al. |
| 2021/0121696 A1 | 4/2021 | Parker et al. |
| 2021/0236821 A1 | 8/2021 | Sinclair et al. |
| 2021/0267523 A1 | 9/2021 | Donoghue et al. |
| 2021/0339014 A1 | 11/2021 | Dinsmoor et al. |
| 2022/0007987 A1* | 1/2022 | Huang .............. A61B 5/4041 |
| 2022/0040486 A1 | 2/2022 | Moffitt |
| 2022/0054090 A1* | 2/2022 | Brockway .............. A61B 5/33 |
| 2022/0111213 A1 | 4/2022 | Cassar et al. |
| 2022/0151535 A1 | 5/2022 | Parker et al. |
| 2022/0218995 A1 | 7/2022 | Block et al. |
| 2022/0233866 A1 | 7/2022 | Gururaj et al. |
| 2022/0266022 A1 | 8/2022 | Steinke et al. |
| 2022/0296892 A1 | 9/2022 | Esteller et al. |
| 2022/0296893 A1 | 9/2022 | Steinke et al. |
| 2022/0339448 A1 | 10/2022 | Jayakumar et al. |
| 2023/0062062 A1 | 3/2023 | Litvak et al. |
| 2023/0069981 A1 | 3/2023 | Isaacson et al. |

(56) References Cited

U.S. PATENT DOCUMENTS

| | | |
|---|---|---|
| 2023/0099390 A1 | 3/2023 | Esteller et al. |
| 2023/0141183 A1 | 5/2023 | Moore et al. |
| 2023/0201597 A1 | 6/2023 | Haddock et al. |
| 2023/0271015 A1 | 8/2023 | Malekmohammadi et al. |

FOREIGN PATENT DOCUMENTS

| | | |
|---|---|---|
| CN | 107280665 A | 10/2017 |
| EP | 3229891 | 8/2019 |
| WO | 2016/205231 A1 | 6/2016 |
| WO | 2018/008034 A2 | 1/2018 |
| WO | 2018/163178 A1 | 9/2018 |
| WO | 2019/070406 A1 | 9/2018 |
| WO | 2018/213872 A1 | 11/2018 |
| WO | 2019/210371 A1 | 5/2019 |
| WO | 2019/211314 A1 | 11/2019 |
| WO | 2019/217079 A1 | 11/2019 |
| WO | 2020/223165 A1 | 11/2020 |
| WO | 2021/026151 | 2/2021 |
| WO | 2021/080727 A1 | 4/2021 |

OTHER PUBLICATIONS

Examination Report No. 1 regarding corresponding Australian Patent Application No. 2022315275, mailed Aug. 5, 2024.
Georgopoulos, Apostolos P., et al., "On the Relations Between the Direction of Two-Dimensional Arm Movements and Cell Discharge in Primate Motor Cortex," The Journal of Neuroscience, vol. 2, No. 11, pp. 1527-1537, 1982.
Hatsopoulos, Nicholas G. et al., "Sensing with the Motor Cortex," J. Neuron, 72(3), 22 pages, 2011.
Shils, Jay, et al., "Motor Evoked Potential Recordings During Segmented DBS—A Feasibility Study," Oper Neurosurg (Hagerstown), Mar. 1, 20215, 20(4), pp. 419-425.
Wiest, C. et al., "Local Field Potential Activity Dynamics in Response to Deep Brain Stimulation of the Subthalamic Nucleus in Parkinson's Disease," Neurobiology of Disease, 143, 2020, 15 pages.
Wiest, C., et al., "Subthalamic Deep Brain Stimulation Induces Finely-Tuned Gamma Oscillations in the Absence of Levodopa," Neurobiology of Disease, 152, 105287, 2021, 13 pages.
Wiest, C., et al., "Local Field Potential Activity Dynamics in Response to Deep Brain Stimulation of the Subthalamic Nucleus in Parkinson's Disease." Neurobiology of Disease, 2019, 41 pages.
U.S. Appl. No. 63/148,740, filed Feb. 12, 2021, Steinke et al.
U.S. Appl. No. 63/162,887, filed Mar. 18, 2021, Esteller et al.
Gmel, Gerrit E., et al., "A New Biomarker for Closed-Loop Deep Brain Stimulation in the Subthalamic Nucleus for Patients with Parkinson's Disease," IEEE Biomedical Circuits and Systems Conference (BioCAS) Proceedings, Lausanne, 2014, pp. 500-503.
Gmel, Gerrit E., et al., "A New Biomarker for Subthalamic Deep Brain Stimulation for Patients with Advanced Parkinson's Disease—A Pilot Study," J. Neural Eng., 12, 2015, 11 pages.
Gmel, Gerrit Eduard, "Evoked Brain Neural Potentials," Dissertation for The University of New South Wales, Sep. 2016, 231 pages.
Kent, Alexander Rafael, et al., "Characterization of Evoked Potentials During Deep Brain Stimulation in the Thalamus," Dissertation Submitted in the Department of Biomedical Engineering Duke University, 2013, 320 pages.
Kent, Alexander R., et al., "Neural Origin of Evoked Potentials During Thalamic Deep Brain Stimulation," J Neurophysiol, 110, 2013, pp. 826-843.
Kent, A.R., et al., "Recording Evoked Potentials During Deep Brain Stimulaton: Development and Validation of Instrumentation to Suppress to Stimulus Artefact," J Neural Eng., 9(3), Jun. 2012, 30 pages.
Kirsch AD, et al., "Anodic Versus Cathodic Neurostimulation of the Subthalamic Nucleus: A Randomized-Controlled Study of Acute Clinical Effects," Parkinsonism and Related Disorders, 55, 2018, pp. 61-67.
Laarne, Paivi, et al., "Accuracy of Two Dipolar Inverse Algorithms Applying Reciprocity for Forward Calculation," Computers and Biomedical Research, vol. 33, Issue 3, pp. 172-185, Jun. 2000.
Moffitt, Michael A., et al., "Electrical Localization of Neural Activity in the Dorsal Horn of the Spinal Cord: A Modeling Study," Annals of Biomedical Engineering, 32(12), pp. 1694-1709, 2004.
Pascual-Marqui, RD, "Standardized Low-Resolution Brain Electromagnetic Tomography (sLORETA): Technical Details," Methods Find Exp Clin Pharmacol, 24 Suppl D, 5-12. 2002.
Sinclair, Nicholas C., et al., "Subthalamic Nucleus Deep Brain Stimulation Evokes Resonant Neural Activity," Annals of Neurology, 83(5), pp. 1027-1031, May 4, 2018.
Sinclair, Nicholas C., et al., "Subthalamic Nucleus Deep Brain Stimulation Evokes Resonant Neural Activity," Poster, 2019, 1 page.
Sinclair, Nicholas C., et al., "Deep Brain Stimulation for Parkinson's Disease Modulates High-Frequency Evoked and Spontaneous Neural Activity," Neurobiology of Disease, vol. 130, 104522, Oct. 2019.
Sinclair, Nicholas C., et al., "On the Neural Basis of Deep Brain Stimulation Evoked Resonant Activity," Biomed. Phys. Eng. Express, 5, 2019, 9 pages.
Sinclair, Nicholas C., et al., "Directional Deep Brain Stimulation Evoked Resonant Neural Activity (ERNA)," Poster, 2020, 1 page.
Thevathasan, Wesley, et al., "Tailoring Subthalamic Nucleus Deep Brain Stimulation for Parkinson's Disease Using Evoked Resonant Neural Activity," Frontiers in Human Neuroscience, vol. 14, Article 71, Feb. 2020, 6 pages.
Walker, Harrison, MD, et al., Directional Subthalamic Nucleus DBS for Parkinson's Disease: Year 3 Interim Analyses, UAB Medicine Poster, 2020, 1 page.
Frankemolle, A.M.M., et al., "Reversing Cognitive-Motor Impairments in Parkinson's Disease Patients Using a Computational Modelling Approach to Deep Brain Stimulation Programming," Brain—A Journal of Neurology, 2010, 133, pp. 746-761.
International Search Report and Written Opinion regarding corresponding PCT Application No. PCT/US2022/073739, mailed Oct. 13, 2022.
Zelmann, Rina, et al., "Automatic Optimization of Depth Electrode Trajectory Planning," Montreal Neurological Institute Neurology and Neurosurgery, CLIP 2013, LNCS 8361, 2014, pp. 99-104.
Beriault, Silvain, et al., "A Multi-Modal Approach to Computer-Assisted Deep Brain Stimulation Trajectory Planning," International Journal of Computer Assisted Radiology and Surgery, 7, 2012, pp. 687-704.
Beriault, Silvain, et al., "A Prospective Evaluation of Computer-Assisted Deep Brain Stimulation Trajectory Planning," Montreal Neurological Institute McConnell Brain Imaging Centre, CLIP 2012, LNCS 7761, 2013, pp. 42-49.

* cited by examiner

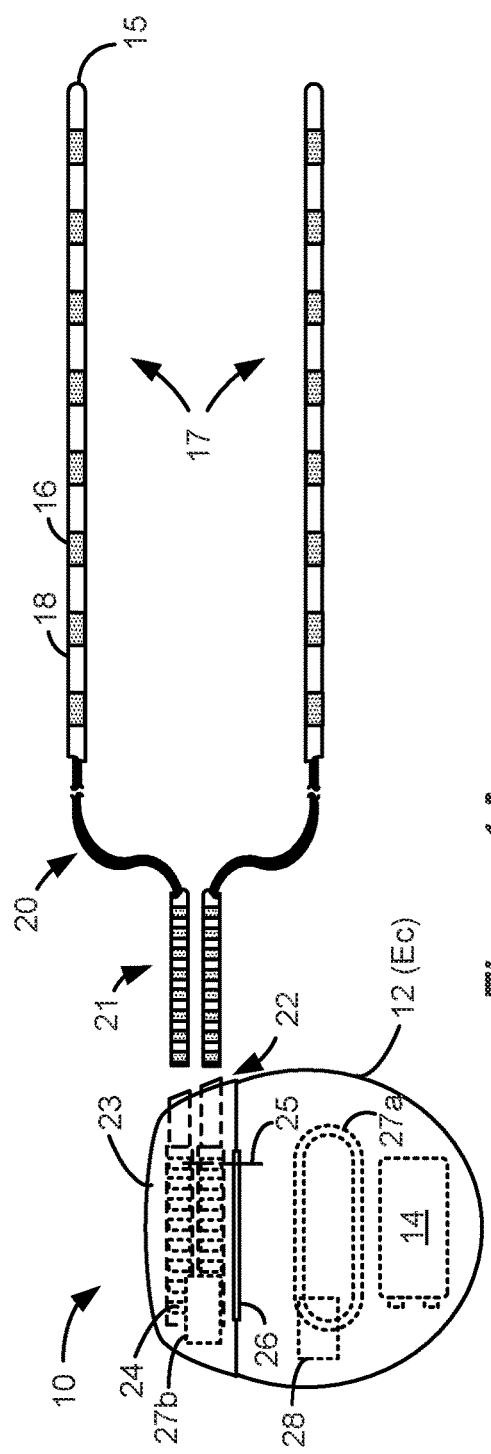
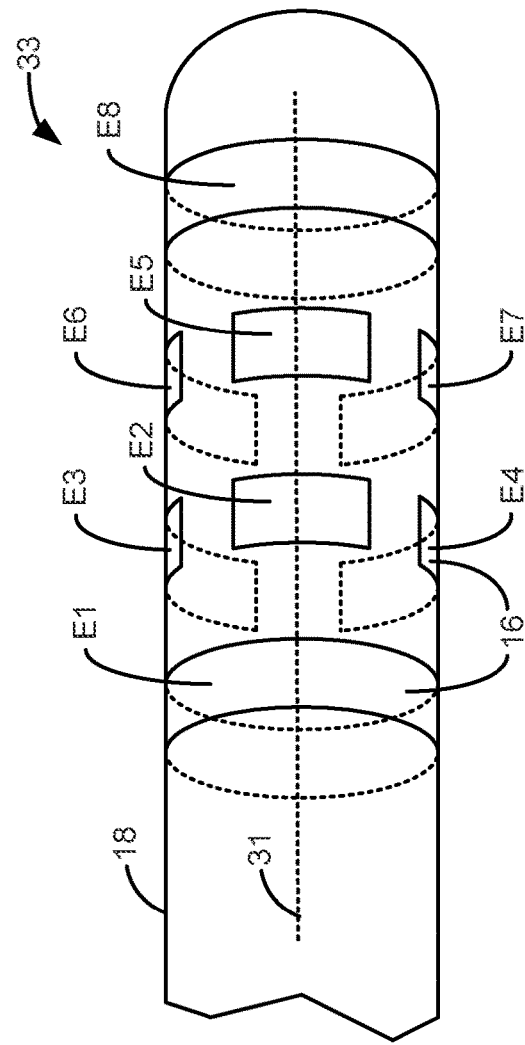
Figure 1A
Figure 1B

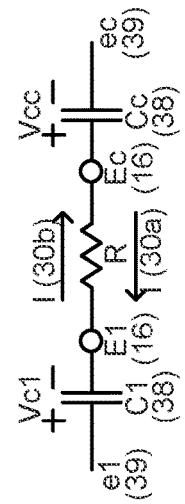
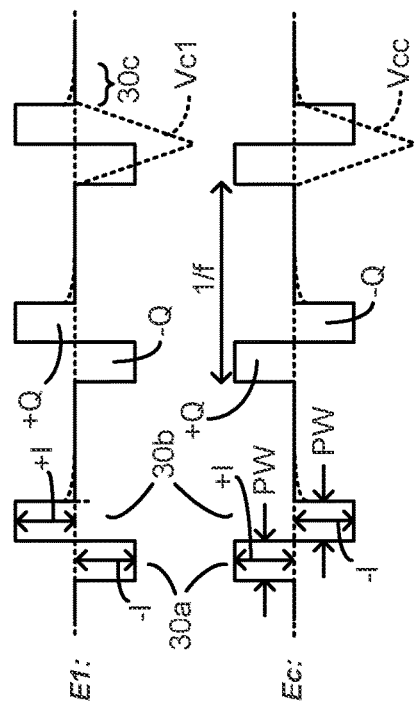
*Figure 2A*
*Figure 2B*
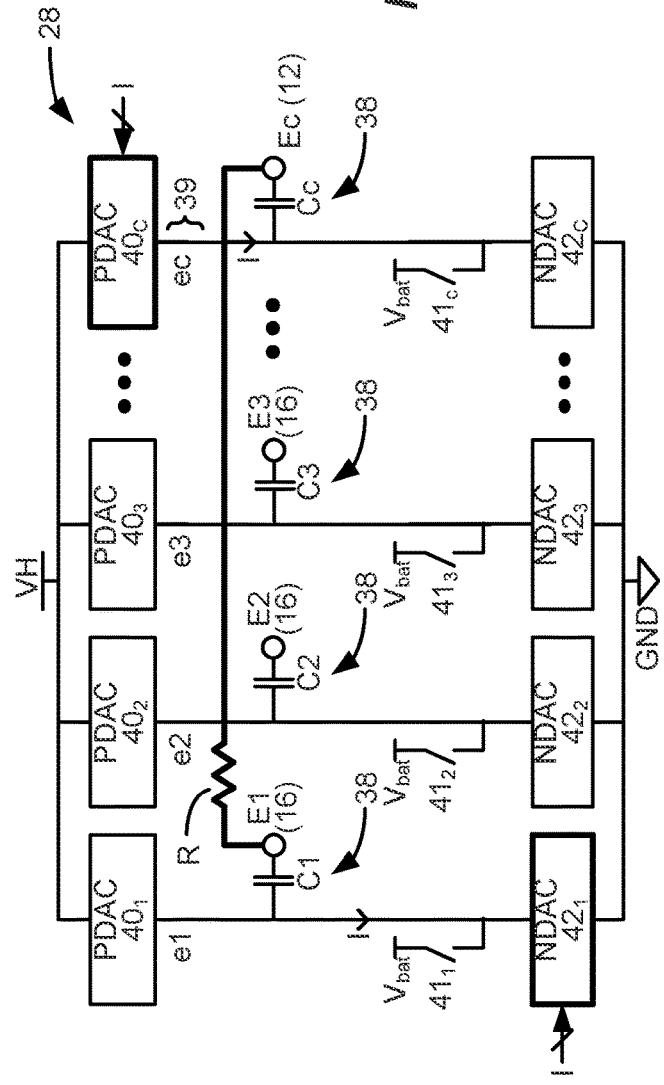
*Figure 3*

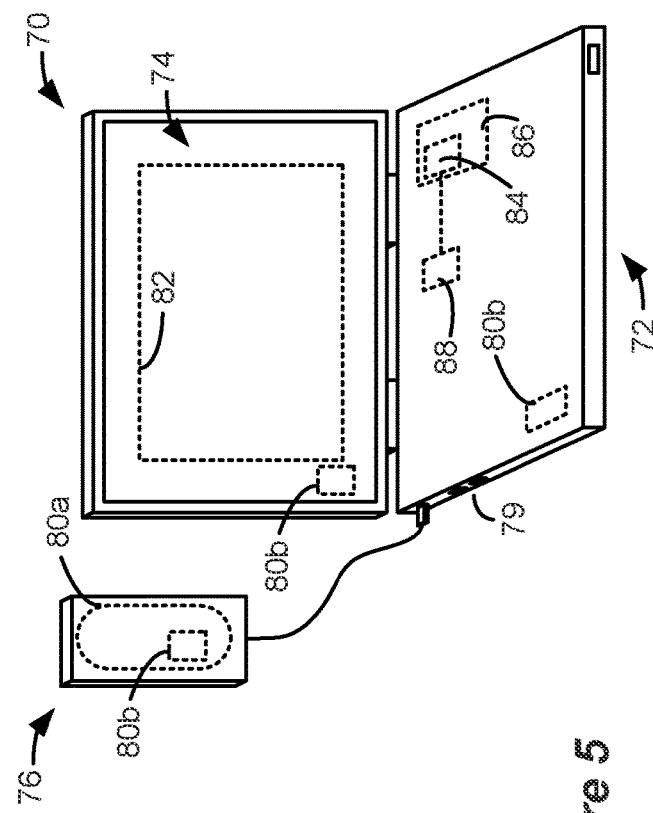
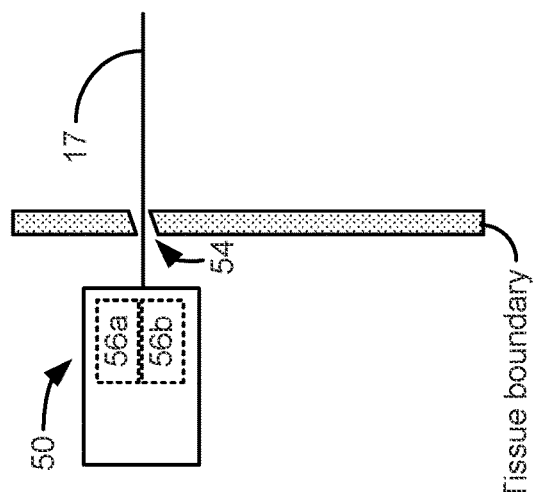
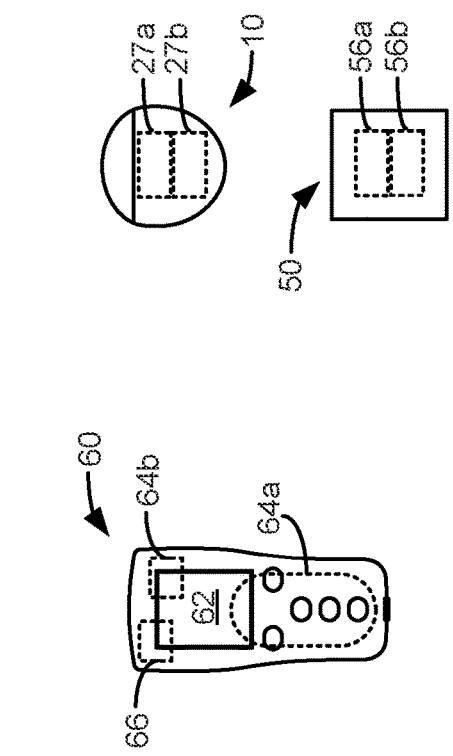

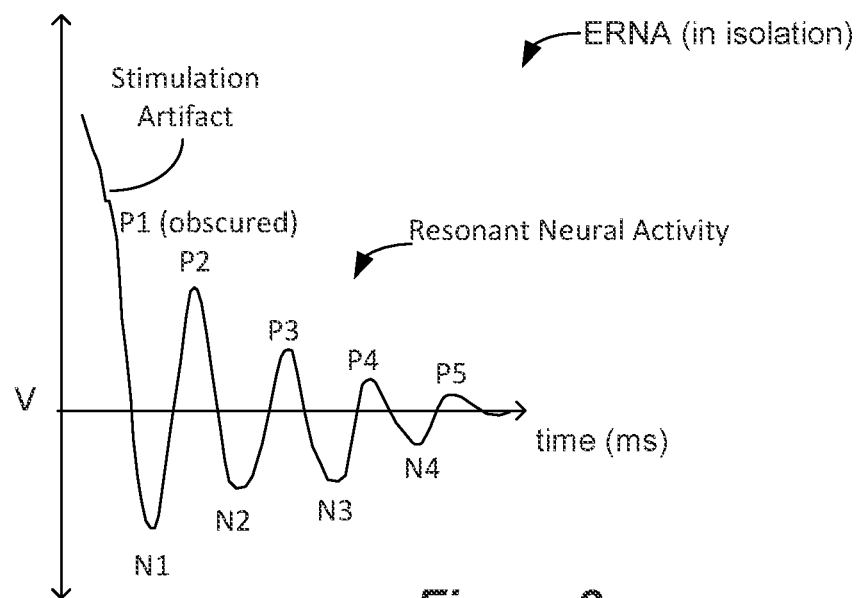
Figure 8
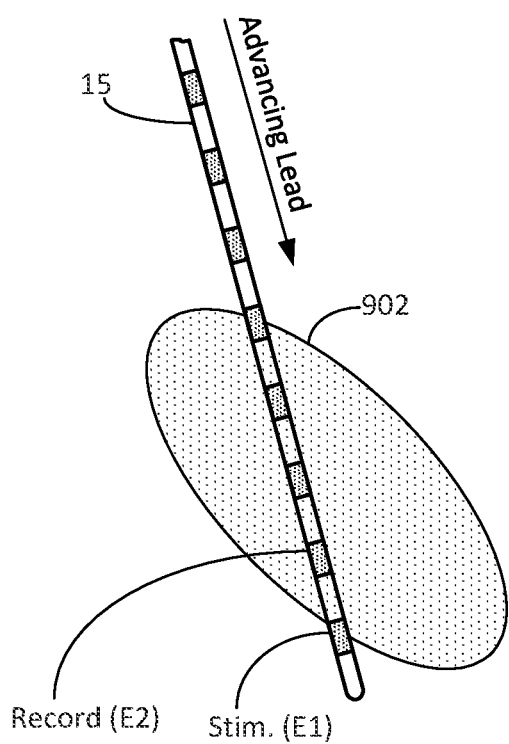
Figure 9
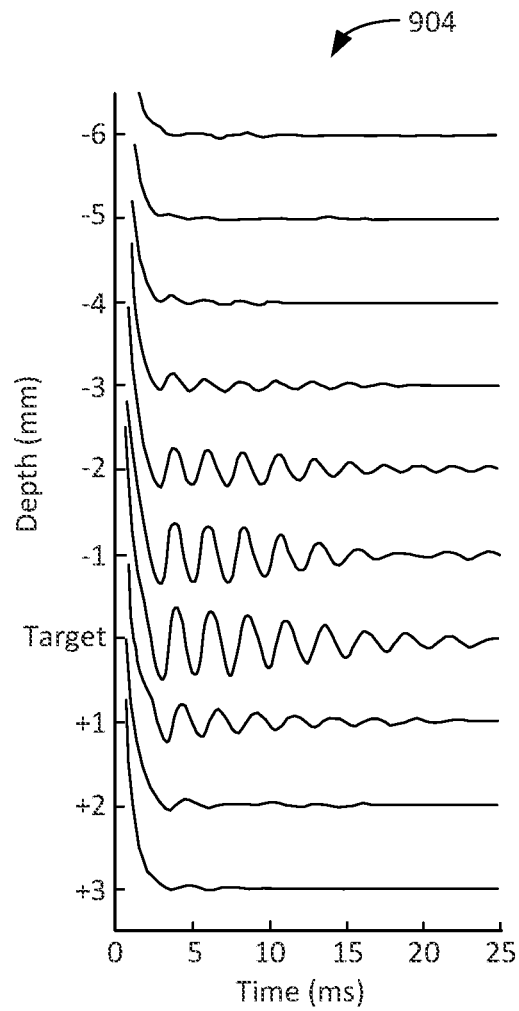

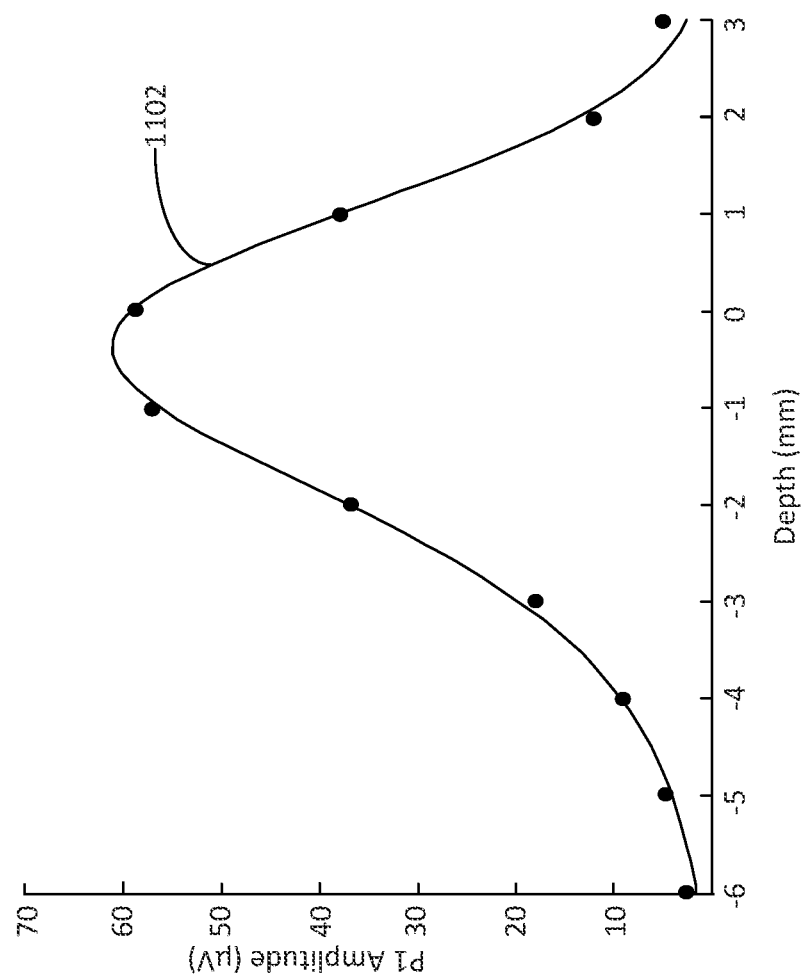
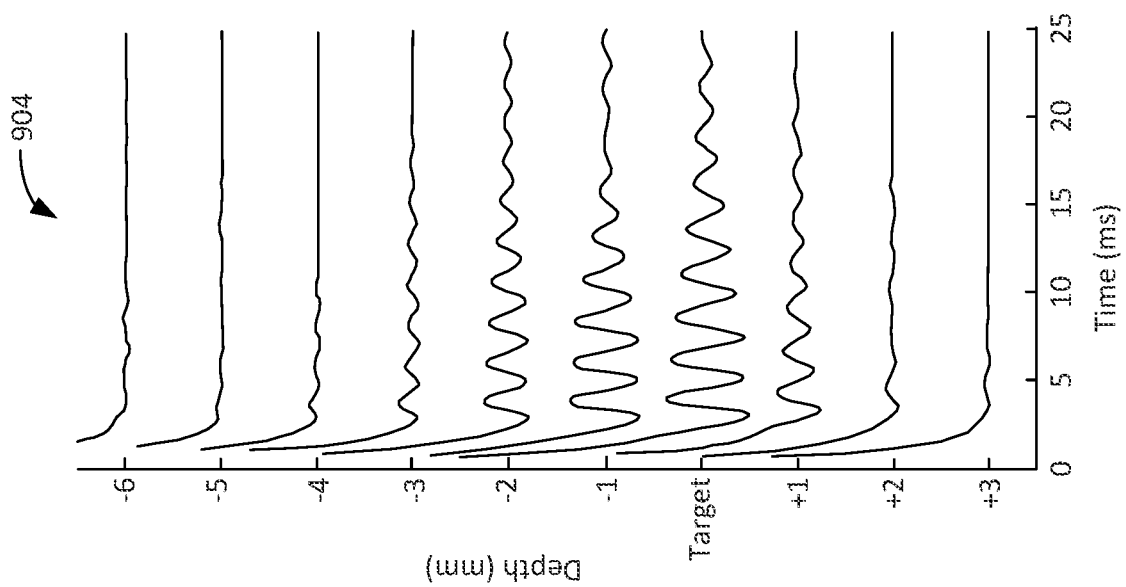
Figure 14

INTERPOLATION METHODS FOR NEURAL RESPONSES

CROSS-REFERENCE TO RELATED APPLICATIONS

This application is a non-provisional application based on U.S. Provisional Patent Application Ser. No. 63/224,751, filed Jul. 22, 2021, which is incorporated herein by reference, and to which priority is claimed.

FIELD OF THE INVENTION

This application relates to deep brain stimulation (DBS), and more particularly, to methods and systems for using sensed neural responses for facilitating aspects of DBS.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS). DBS has been applied therapeutically for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707. However, the present invention may find applicability with any implantable neurostimulator device system.

Each of these neurostimulation systems, whether implantable or external, typically includes one or more electrode carrying stimulation leads, which are implanted at the desired stimulation site, and a neurostimulator, used externally or implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of movement disorders), while minimizing the volume of non-target tissue that is stimulated. A typical stimulation parameter set may include the electrodes that are acting as anodes or cathodes, as well as the amplitude, duration, and rate of the stimulation pulses.

Non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects. For example, bilateral DBS of the subthalamic nucleus has been shown to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., Reversing Cognitive-Motor Impairments in Parkinson's Disease Patients Using a Computational Modelling Approach to Deep Brain Stimulation Programming, Brain 2010; pp. 1-16). In large part, this phenomenon is due to the small size of the subthalamic nucleus. Even with the electrodes are located predominately within the sensorimotor territory, the electrical field generated by DBS is non-discriminately applied to all neural elements surrounding the electrodes, thereby resulting in the spread of current to neural elements affecting cognition. As a result, diminished cognitive function during stimulation of the subthalamic nucleus may occur do to non-selective activation of non-motor pathways within or around the subthalamic nucleus.

The large number of electrodes available, combined with the ability to generate a variety of complex stimulation pulses, presents a huge selection of stimulation parameter sets to the clinician or patient. In the context of DBS, neurostimulation leads with a complex arrangement of electrodes that not only are distributed axially along the leads, but are also distributed circumferentially around the neurostimulation leads as segmented electrodes, can be used.

To facilitate such selection, the clinician generally programs the external control device, and if applicable the neurostimulator, through a computerized programming system. This programming system can be a self-contained hardware/software system, or can be defined predominantly by software running on a standard personal computer (PC) or mobile platform. The PC or custom hardware may actively control the characteristics of the electrical stimulation generated by the neurostimulator to allow the optimum stimulation parameters to be determined based on patient feedback, including both, but not limited to, behavioral and clinical response, anatomical and neurophysiological information and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. The system may also instruct the user how to improve the positioning of the leads, or confirm when a lead is well-positioned. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

In the context of DBS, the brain is dynamic (e.g., due to disease progression, motor re-learning, pneumocephalus (brain shift) during implantation surgical procedure, the development of scar tissue in the region of the implanted leads, or other changes), and a program (i.e., a set of stimulation parameters) that is useful for a period of time may not maintain its effectiveness and/or the expectations of the patient may increase. Further, physicians typically treat the patient with stimulation and medication, and proper amounts of each are required for optimal therapy. In particular, a patient's stimulation needs may be impacted by their medication state. Additionally, the need for stimulation and/or medication may fluctuate across the day and week, depending on activities of daily living, especially sleep and activity. Moreover, brain diseases treated by DBS, such as Parkinson's disease, may be multi-faceted with respect to their symptomatic profiles (for example rigidity vs tremor in Parkinson disease), and optimal treatments may be different when addressing one symptom to another.

Thus, there is a need for methods and systems that assist a clinician in obtaining an optimum lead placement during implantation process and to determine optimum stimulation parameters for treating the patient. There is also a need for closed loop feedback that can be used to adjust stimulation parameters as the patient's stimulation needs change with time or based on their medication state.

SUMMARY

Disclosed herein is a method of monitoring neural activity in a patient's brain, using one or more electrode leads in the patient's brain, wherein each electrode lead comprises a plurality of electrodes, each of which may be configured for stimulating or recording, the method comprising: recording a plurality of signals each indicative of neural activity in the patient's brain using one or more of the electrodes, for each signal, determining if the signal or portion thereof is corrupted, determining values for one or more waveform features for each of the plurality of signals or portions that is not corrupted, and interpolating values for one or more waveform features for each of the corrupted signals, wherein the interpolating comprises using the waveform feature values determined for the non-corrupted signals. According to some embodiments, the method further comprises providing electrical stimulation to the patient's brain using one or more of the electrodes, and wherein the neural activity is evoked by the electrical stimulation. According to some embodiments, the plurality of signals are each time-varying signals. According to some embodiments, determining if the signal is corrupted comprises determining if one or more waveform feature values derived from the signal are outside a predetermined range. According to some embodiments, determining if the signal or portion is corrupted comprises matching the signal with one or more template signals or portions, wherein the template signal corresponds to a prior or an expected neural response. According to some embodiments, the expected neural response comprises an evoked resonant neural response (ERNA). According to some embodiments, determining if the signal is corrupted comprises converting the signal from a time domain signal to a frequency domain signal. According to some embodiments, the method further comprises determining if the frequency domain signal comprises one or more frequency components corresponding to frequency components characteristic of a known neural response. According to some embodiments, the plurality of signals comprises signals recorded at different positions within the patient's brain. According to some embodiments, the plurality of signals are recorded at different positions within the patient's brain as the electrode lead position is adjusted within the patient's brain. According to some embodiments, each of the plurality of signals are recorded at different electrodes. According to some embodiments, the interpolating comprises fitting the values for the one or more waveform features for each of the plurality of signals that is not corrupted to a model and using the model to interpolate the values for the one or more waveform features for each of the corrupted signals. According to some embodiments, the model is a Gaussian function or a spline function. According to some embodiments, the model expresses the value of the one or more waveform features as a function of spatial position and/or orientation within the brain. According to some embodiments, the one or more waveform features are selected from the group consisting of amplitudes of any peaks, peak-to-peak height between any two peaks, a ratio of heights of any two peaks, and an area under any one or more peaks. According to some embodiments, one or more of the second electrodes are directional electrodes.

Also disclosed herein is a medical device configured to monitor neural activity evoked by electrical stimulation in a patient's brain, wherein the electrical stimulation is provided by one or more electrode leads configurable to be placed in the patient's brain, wherein each electrode lead comprises a plurality of electrodes, each of which may be configured for stimulating or recording, the device comprising: control circuitry configured to: cause a first one or more of the electrodes to provide stimulation to the patient's brain, cause a second one or more of the electrodes to record a plurality of signals each indicative of neural activity evoked in the patient's brain, for each signal, determine if the signal or a portion thereof is corrupted, determine values for one or more waveform features for each of the plurality of signals that is not corrupted, and interpolate values for one or more waveform features for each of the corrupted signals, wherein the interpolating comprises using the waveform feature values determined for the non-corrupted signals. According to some embodiments, the device is a clinician programmer (CP). According to some embodiments, the device is an implantable pulse generator (IPG). According to some embodiments, the device is an external trial stimulator (ETS). According to some embodiments, the plurality of signals are each time-varying signals. According to some embodiments, determining if the signal is corrupted comprises determining if one or more waveform feature values derived from the signal are outside a predetermined range. According to some embodiments, determining if the signal or portion is corrupted comprises matching the signal with one or more template signals or portions, wherein the template signal corresponds to a prior or an expected neural response. According to some embodiments, the expected neural response comprises an evoked resonant neural response (ERNA). According to some embodiments, determining if the signal is corrupted comprises converting the signal from a time domain signal to a frequency domain signal. According to some embodiments, determining if the signal is corrupted comprises determining if the frequency domain signal comprises one or more frequency components corresponding to frequency components characteristic of a known neural response. According to some embodiments, the plurality of signals comprises signals recorded at different of positions within the patient's brain. According to some embodiments, the plurality of signals are recorded at different positions within the patient's brain as the electrode lead position is adjusted within the patient's brain. According to some embodiments, the plurality of signals are recorded at different electrodes. According to some embodiments, the interpolating comprises fitting the values for the one or more waveform features for each of the plurality of signals that is not corrupted to a model and using the model to interpolate the values for the one or more waveform features for each of the corrupted signals. According to some embodiments, the model is a Gaussian function or a spline function. According to some embodiments, the model expresses the value of the one or more waveform features as a function of spatial position and/or orientation within the brain. According to some embodiments, the one or more waveform features are selected from the group consisting of amplitudes of any peaks, peak-to-peak height between any two peaks, a ratio of heights of any two peaks, and an area under any one or more peaks.

Also disclosed herein is a method of monitoring neural activity in a patient's brain, using one or more electrode leads in the patient's brain, wherein each electrode lead comprises a plurality of electrodes, each of which may be configured for stimulating or recording, the method comprising: recording a plurality of signals each indicative of neural activity in the patient's brain using one or more of the electrodes, for each signal, determining if a portion of the signal is corrupted, if a portion of the signal is corrupted interpolating values for the corrupted portion using uncorrupted portions of the corrupted signal and/or using uncorrupted signals. According to some embodiments, the method further comprises providing electrical stimulation to the patient's brain using one or more of the electrodes, and wherein the neural activity is evoked by the electrical stimulation. According to some embodiments, the plurality of signals are each time-varying signals. According to some embodiments, determining if the signal is corrupted comprises determining if one or more waveform feature values derived from the signal are outside a predetermined range. According to some embodiments, the interpolating comprises fitting the values for the one or more waveform features for each of the plurality of signals that is not corrupted to a model and using the model to interpolate the values for the one or more waveform features for each of the corrupted signals. According to some embodiments, the model is a Gaussian function or a spline function. According to some embodiments, the model expresses the value of the one or more waveform features as a function of spatial position and/or orientation within the brain. According to some embodiments, the one or more waveform features are selected from the group consisting of amplitudes of any peaks, peak-to-peak height between any two peaks, a ratio of heights of any two peaks, and an area under any one or more peaks. According to some embodiments, determining if the signal or portion is corrupted comprises matching the signal with one or more template signals or portions, wherein the template signal corresponds to a prior or an expected neural response. According to some embodiments, the expected neural response comprises an evoked resonant neural response (ERNA). According to some embodiments, determining if the signal is corrupted comprises converting the signal from a time domain signal to a frequency domain signal. According to some embodiments, the method further comprises determining if the frequency domain signal comprises one or more frequency components corresponding to frequency components characteristic of a known neural response. According to some embodiments, the plurality of signals comprises signals recorded at different of positions within the patient's brain. According to some embodiments, the plurality of signals are recorded at different positions within the patient's brain as the electrode lead position is adjusted within the patient's brain. According to some embodiments, each of the plurality of signals are recorded at different electrodes. Also disclosed herein is a medical device configured to perform the above methods.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS. The invention may also reside in one or more non-transitory computer-readable media comprising instructions, which when executed by a processor of a machine configure the machine to perform any of the above methods.

BRIEF DESCRIPTION OF THE DRAWINGS

FIG. 1A shows an Implantable Pulse Generator (IPG).

FIG. 1B shows a percutaneous lead having split-ring directional electrodes.

FIGS. 2A and 2B show an example of stimulation pulses (waveforms) producible by the IPG or by an External Trial Stimulator (ETS).

FIG. 3 shows an example of stimulation circuitry useable in the IPG or ETS.

FIG. 4 shows an ETS environment useable to provide stimulation before implantation of an IPG.

FIG. 5 shows various external devices capable of communicating with and programming stimulation in an IPG or ETS.

FIG. 8 illustrates an evoked resonant neural response (ERNA) in isolation.

FIG. 9 illustrates a series of neural response signals recorded as an electrode lead is advanced through a patient's brain.

FIG. 14 illustrates a series of recorded neural response signals having extracted waveform features fit to a curve useful for interpolating waveform features for recorded neural response signals that are corrupted.

DETAILED DESCRIPTION

Figure 6:
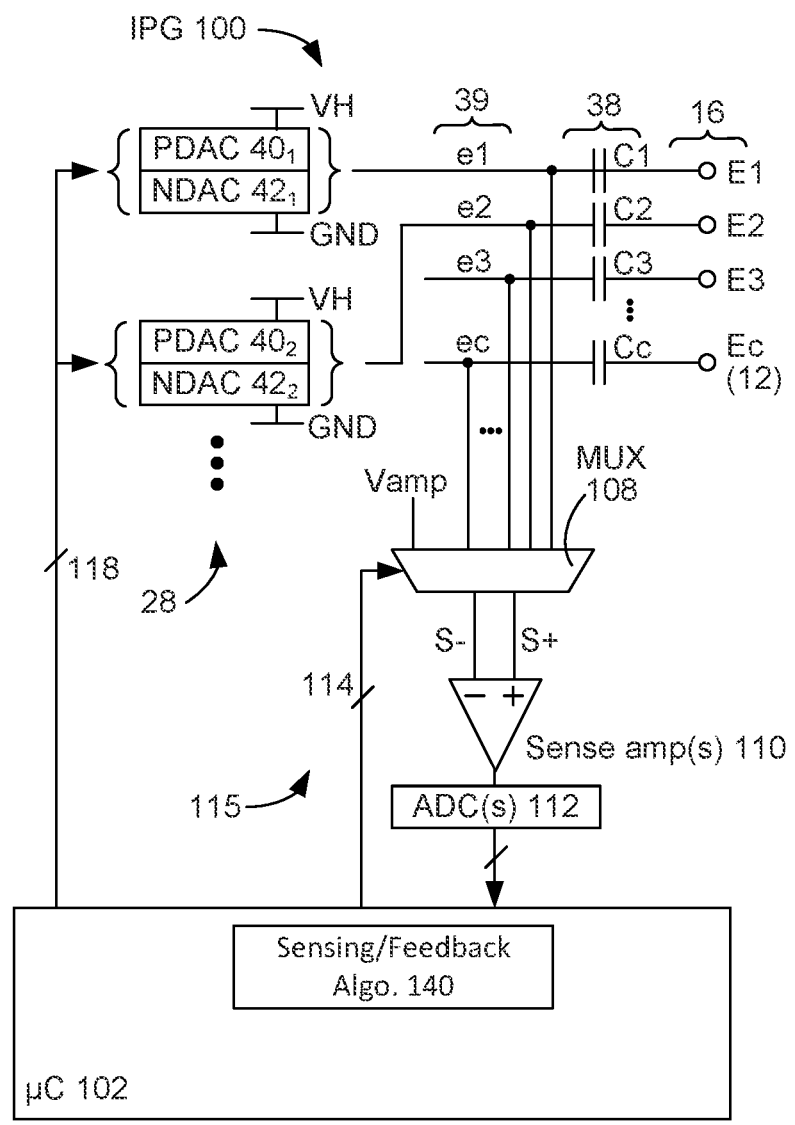
FIG. 6 illustrates sensing circuitry useable in an IPG.

An implantable neurostimulator system, such as a DBS system, typically includes an Implantable Pulse Generator (IPG) 10 shown in FIG. 1A. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more electrode leads 15 can be used having ring-shaped electrodes 16 carried on a flexible body 18.

In yet another example shown in FIG. 1B, an electrode lead 33 can include one or more split-ring electrodes. In this example, eight electrodes 16 (E1-E8) are shown, though the number of electrodes may vary. Electrode E8 at the distal end of the lead and electrode E1 at a proximal end of the lead comprise ring electrodes spanning 360 degrees around a central axis of the lead 33. Electrodes E2, E3, and E4 comprise split-ring directional electrodes, each of which are located at the same longitudinal position along the central axis 31, but with each spanning less than 360 degrees around the axis. For example, each of electrodes E2, E3, and E4 may span 90 degrees around the axis 31, with each being separated from the others by gaps of 30 degrees. Electrodes E5, E6, and E7 also comprise split-ring directional electrodes, but are located at a different longitudinal position along the central axis 31 than are split ring electrodes E2, E3, and E4. As shown, the split-ring directional electrodes E2-E4 and E5-E7 may be located at longitudinal positions along the axis 31 between ring electrodes E1 and E8. However, this is just one example of a lead 33 having split-ring electrodes. In other designs, all electrodes can be split-ring, or there could be different numbers of split-ring electrodes at each longitudinal position (i.e., more or less than three), or the ring and split-ring electrodes could occur at different or random longitudinal positions, etc.

Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are sixteen electrodes (E1-E16), split between two percutaneous leads 15 (or contained on a single paddle lead, not shown) and thus the header 23 may include a 2×2 array of eight-electrode lead connectors 22. However, the type and number of leads, and the number of electrodes, in an IPG is application specific and therefore can vary. The conductive case 12 can also comprise an electrode (Ec).

In a DBS application, as is useful in the treatment of movement symptoms in Parkinson's disease for example, the IPG 10 is typically implanted under the patient's clavicle (collarbone). Lead wires 20 are tunneled through the neck and the scalp and the electrode leads 15 (or 33) are implanted through holes drilled in the skull and positioned for example in the subthalamic nucleus (STN) and the Globus pallidus internus (GPi) in each brain hemisphere.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1A, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Bluetooth Low Energy (BLE), as described in U.S. Patent Publication 2019/0209851, Zigbee, WiFi, MICS, and the like.

Stimulation in IPG 10 is typically provided by electrical pulses each of which may include a number of phases such as 30a and 30b, as shown in the example of FIG. 2A. In the example shown, such stimulation is monopolar, meaning that a current is provided between at least one selected lead-based electrode (e.g., E1) and the case electrode Ec 12. Stimulation parameters typically include amplitude (current I, although a voltage amplitude V can also be used); frequency (f); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30a), and thus provides pulses which sink a negative current of amplitude −I from the tissue. The case electrode Ec has been selected as an anode (again during first phase 30a), and thus provides pulses which source a corresponding positive current of amplitude +I to the tissue. Note that at any time the current sunk from the tissue (e.g., −I at E1 during phase 30a) equals the current sourced to the tissue (e.g., +I at Ec during phase 30a) to ensure that the net current injected into the tissue is zero. The polarity of the currents at these electrodes can be changed: Ec can be selected as a cathode, and E1 can be selected as an anode, etc.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node Ei 39. Each electrode node Ei 39 is connected to an electrode Ei 16 via a DC-blocking capacitor Ci 38, for the reasons explained below. PDACs $40_i$ and NDACs $42_i$ can also comprise voltage sources.

Proper control of the PDACs $40_i$ and NDACs $42_i$ allows any of the electrodes 16 and the case electrode Ec 12 to act as anodes or cathodes to create a current through a patient's tissue, R, hopefully with good therapeutic effect. In the example shown, and consistent with the first pulse phase 30a of FIG. 2A, electrode E1 has been selected as a cathode electrode to sink current from the tissue R and case electrode Ec has been selected as an anode electrode to source current to the tissue R. Thus, PDAC $40_C$ and NDAC $42_1$ are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. Patent Application Publication 2013/0289665.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publications 2018/0071520 and 2019/0083796. The stimulation circuitries described herein provide multiple independent current control (MICC) (or multiple independent voltage control) to guide the estimate of current fractionalization among multiple electrodes and estimate a total amplitude that provides a desired strength. In other words, the total anodic current can be split among two or more electrodes and/or the total cathodic current can be split among two or more electrodes, allowing the stimulation location and resulting field shapes to be adjusted. For example, a "virtual electrode" may be created at a position between two physical electrodes by fractionating current between the two electrodes. In other words, the virtual electrode is not co-located with any of the physical electrodes. Appreciate, that in the context of split ring electrodes, such as electrodes E2-E4 (FIG. 1B), current fractionating can be used to create a virtual electrode at a rotational angle that is between two physical split ring electrodes (e.g., between E2 and E3). Accordingly, current fractionalization can be used to provide stimulation at any location along the lead and at any rotational angle about the lead. Note also that split ring electrodes at a given longitudinal position on the lead can be "ganged" together to effectively create a ring electrode at that position.

Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27a and/or 27b), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30a, charge will build up across the DC-blockings capacitors C1 and Cc associated with the electrodes E1 and Ec used to produce the current, giving rise to voltages Vc1 and Vcc which decrease in accordance with the amplitude of the current and the capacitance of the capacitors 38 (dV/dt=I/C). During the second pulse phase 30b, when the polarity of the current I is reversed at the selected electrodes E1 and Ec, the stored charge on capacitors C1 and Cc is actively recovered, and thus voltages Vc1 and Vcc increase and return to 0V at the end the second pulse phase 30b.

To recover all charge by the end of the second pulse phase 30b of each pulse (Vc1=Vcc=0V), the first and second phases 30a and 30b are charged balanced at each electrode, with the first pulse phase 30a providing a charge of $-Q$ ($-I*PW$) and the second pulse phase 30b providing a charge of $+Q$ ($+I*PW$) at electrode E1, and with the first pulse phase 30a providing a charge of $+Q$ and the second pulse phase 30b providing a charge of $-Q$ at the case electrode Ec. In the example shown, such charge balancing is achieved by using the same pulse width (PW) and the same amplitude (|I|) for each of the opposite-polarity pulse phases 30a and 30b. However, the pulse phases 30a and 30b may also be charged balance at each electrode if the product of the amplitude and pulse widths of the two phases 30a and 30b are equal, or if the area under each of the phases is equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes ei 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced.

Therefore, and as shown in FIG. 2A, passive charge recovery typically occurs after the issuance of second pulse phases 30b, for example during at least a portion 30c of the quiet periods between the pulses, by closing passive recovery switches $41_i$. As shown in FIG. 3, the other end of the switches $41_i$ not coupled to the electrode nodes ei 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 by placing the capacitors in parallel between the reference voltage (Vbat) and the patient's tissue. Note that passive charge recovery is illustrated as small exponentially decaying curves during 30c in FIG. 2A, which may be positive or negative depending on whether pulse phase 30a or 30b have a predominance of charge at a given electrode.

Passive charge recovery 30c may alleviate the need to use biphasic pulses for charge recovery, especially in the DBS context when the amplitudes of currents may be lower, and therefore charge recovery less of a concern. For example, and although not shown in FIG. 2A, the pulses provided to the tissue may be monophasic, comprising only a first pulse phase 30a. This may be followed thereafter by passive charge recovery 30c to eliminate any charge build up that occurred during the singular pulses 30a. Monophasic pulses may be either cathodic or anodic.

FIG. 4 shows an external trial stimulation (ETS) that may be used prior to implantation of an IPG 10 in a patient, for example, in the operating room to test stimulation and confirm the lead position. During external trial stimulation, stimulation can be tried on the implant patient to evaluate therapeutic and side-effect thresholds and confirm that the lead is not too close to structures that cause side effects. Note that the term ETS, as used herein, refers broadly to any non-implanted device used to control the implanted leads to deliver stimulation, whether during the surgical implantation of the leads, during a fitting/programming session, etc. Like the IPG 10, the ETS 50 can include one or more antennas to enable bi-directional communications with external devices such as those shown in FIG. 5. Such antennas can include a near-field magnetic-induction coil antenna 56a, and/or a far-field RF antenna 56b, as described earlier. ETS 50 may also include stimulation circuitry able to form stimulation in accordance with a stimulation program, which circuitry may be similar to or comprise the same stimulation circuitry 28 (FIG. 3) present in the IPG 10. ETS 50 may also include a battery (not shown) for operational power. The sensing capabilities described herein with regard to the IPG 10, may also be included in the ETS 50 for the purposes described below. As the IPG may include a case electrode, an ETS may provide one or more connections to establish similar returns; for example, using patch electrodes. Likewise, the ETS may communicate with the clinician programmer (CP) 70 so that the CP can process the data as described below.

FIG. 5 shows various external devices that can wirelessly communicate data with the IPG 10 and/or ETS 50, including a patient hand-held external controller 60, and a clinician programmer (CP) 70. Both of devices 60 and 70 can be used to wirelessly transmit a stimulation program to the IPG 10 or ETS 50—that is, to program their stimulation circuitries to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10 or ETS 50, such as various status information, etc.

External controller 60 can be as described in U.S. Patent Application Publication 2015/0080982 for example and may comprise a controller dedicated to work with the IPG 10 or ETS 50. External controller 60 may also comprise a general-purpose mobile electronics device such as a mobile phone, tablet, or other computing device that has been programmed with a Medical Device Application (MDA) allowing it to work as a wireless controller for the IPG 10 or ETS, as described in U.S. Patent Application Publication 2015/0231402. External controller 60 includes a user interface, preferably including means for entering commands (e.g., buttons or selectable graphical elements) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64a capable of wirelessly communicating with the coil antenna 27a or 56a in the IPG 10 or ETS 50. The external controller 60 can also have a far-field RF antenna 64b capable of wirelessly communicating with the RF antenna 27b or 56b in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27a or 56a, wand 76 can likewise include a coil antenna 80a to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27b or 56b, the wand 76, the computing device 72, or both, can likewise include an RF antenna 80b to establish communication at larger distances, as described above. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at www.intel.com. Such control circuitry 88, in addition to executing the clinician programmer software 84 and rendering the GUI 82, can also enable communications via antennas 80a or 80b to communicate stimulation parameters chosen through the GUI 82 to the patient's IPG 10.

The user interface of the external controller 60 may provide similar functionality because the external controller 60 can include similar hardware and software programming as the clinician programmer. For example, the external controller 60 includes control circuitry 66 similar to the control circuitry 88 in the clinician programmer 70 and may similarly be programmed with external controller software stored in device memory.

An increasingly interesting development in pulse generator systems is the addition of sensing capability to complement the stimulation that such systems provide. FIG. 6 shows an IPG 100 that includes stimulation and sensing functionality. (An ETS as described earlier could also include stimulation and sensing capabilities). FIG. 6 shows further details of the circuitry in an IPG 100 that can provide stimulation and sensing spontaneous or evoked signals. The IPG 100 includes control circuitry 102, which may comprise a microcontroller, such as Part Number MSP430, manufactured by Texas Instruments, Inc., which is described in data sheets at www.ti.com, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier. The control circuitry 102 may be configured with one or more sensing/feedback algorithms 140 that are configured to cause the IPG to make certain adjustments and/or take certain actions based on the sensed neural signals.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 to one or more PDACs $40_i$ or NDACs $42_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present but are not shown in FIG. 6 for simplicity. Stimulation parameters used to evoke recordable signals may be similar or different from stimulation delivered for therapeutic purposes, including the details of the pulse phases, such as the order and duration of active and passive phases. These may be designed to reduce recorded artifact, and interpolation methods may consider these evoking stimulus pulse details.

IPG 100 also includes sensing circuitry 115, and one or more of the electrodes 16 can be used to sense spontaneous or evoked electrical signals, e.g., biopotentials from the patient's tissue. In this regard, each electrode node 39 can further be coupled to a sense amp circuit 110. Under control by bus 114, a multiplexer 108 can select one or more electrodes to operate as sensing electrodes (S+, S−) by coupling the electrode(s) to the sense amps circuit 110 at a given time, as explained further below. Although only one multiplexer 108 and sense amp circuit 110 are shown in FIG. 6, there could be more than one. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S− to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the signals being sensed will still readily be sensed by the sense amp circuitry 110. In other examples, signals may be sensed directly at the electrodes 16 without passage through intervening capacitors 38.

According to some embodiments, it may be preferred to sense signals differentially, and in this regard, the sense amp circuitry 110 comprises a differential amplifier receiving the sensed signal S+ (e.g., E3) at its non-inverting input and the sensing reference S− (e.g., E1) at its inverting input. As one skilled in the art understands, the differential amplifier will subtract S− from S+ at its output, and so will cancel out any common mode voltage from both inputs. This can be useful for example when sensing various neural signals, as it may be useful to subtract the relatively large-scale stimulation artifact from the measurement (as much as possible). Examples of sense amp circuitry 110, and manner in which such circuitry can be used, can be found in U.S. Patent Application Publications 2019/0299006, 2020/0305744, 2020/0305745, and 2022/0233866. The IPG (and/or ETS) may also be configured to determine impedances at any of the electrodes. For example, the IPG (and/or ETS) may be configured with sample and hold circuitry, controlled by the control circuitry for measuring impedances.

Figure 7:
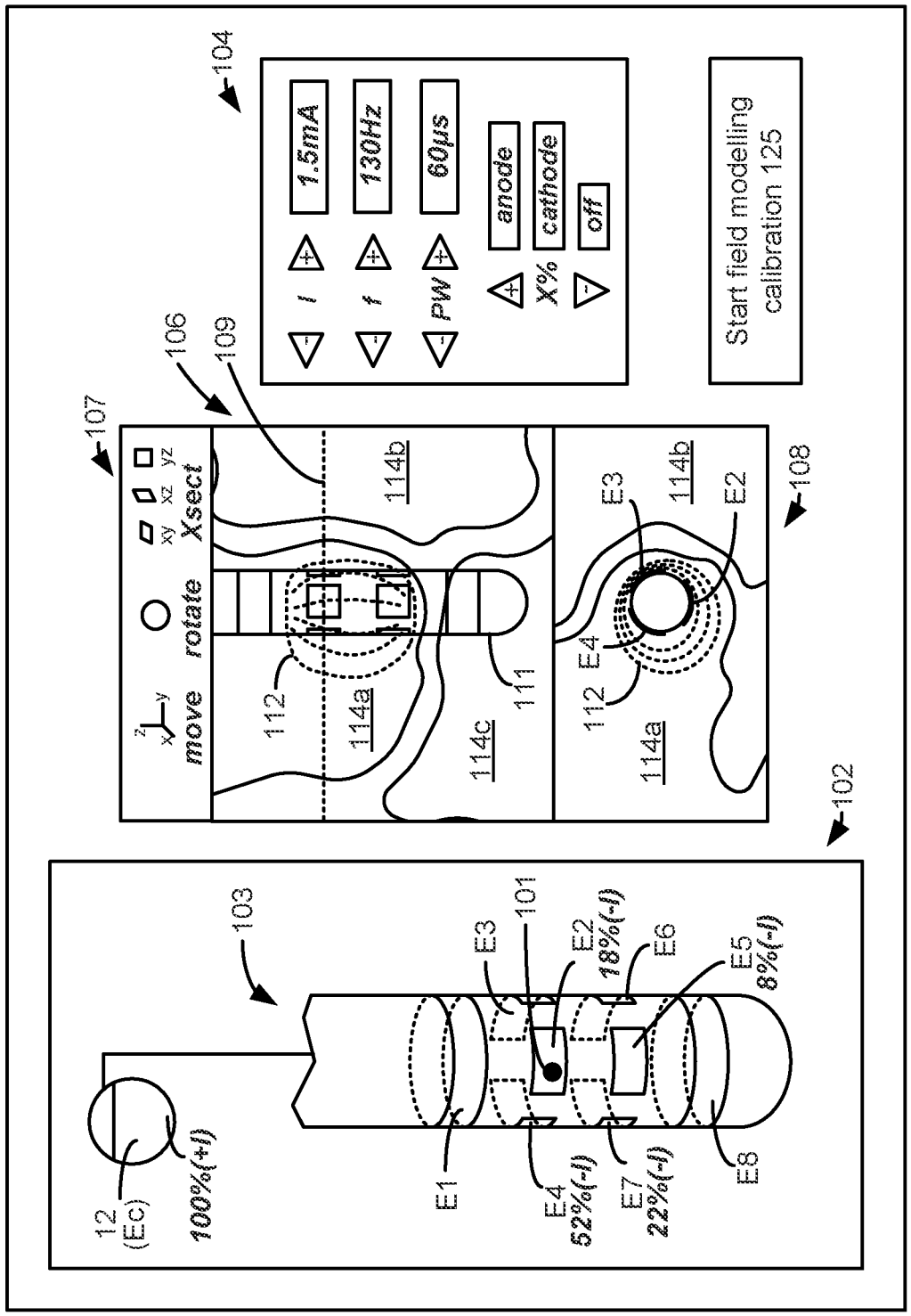
FIG. 7 illustrates an embodiment of a user interface (UI) for programming stimulation.

Particularly in the DBS context, it can be useful to provide a clinician with a visual indication of how stimulation selected for a patient will interact with the tissue in which the electrodes are implanted. This is illustrated in FIG. 7, which shows a Graphical User Interface (GUI) 100 operable on an external device capable of communicating with an IPG 110 or ETS 150. Typically, and as assumed in the description that follows, GUI 100 would be rendered on a clinician programmer 70 (FIG. 5), which may be used during surgical implantation of the leads, or after implantation when a therapeutically useful stimulation program is being chosen for a patient. However, GUI 100 could be rendered on a patient external programmer 60 (FIG. 5) or any other external device capable of communicating with the IPG 110 or ETS 150.

GUI 100 allows a clinician (or patient) to select the stimulation program that the IPG 110 or ETS 150 will provide and provides options that control sensing of spontaneous or evoked responses, as described below. In this regard, the GUI 100 may include a stimulation parameter interface 104 where various aspects of the stimulation program can be selected or adjusted. For example, interface 104 allows a user to select the amplitude (e.g., a current I) for stimulation; the frequency (f) of stimulation pulses; and the pulse width (PW) of the stimulation pulses. Stimulation parameter interface 104 can be significantly more complicated, particularly if the IPG 100 or ETS 150 supports the provision of stimulation that is more complicated than a repeating sequence of pulses. See, e.g., U.S. Patent Application Publication 2018/0071513. Nonetheless, interface 104 is simply shown for simplicity in FIG. 7 as allowing only for amplitude, frequency, and pulse width adjustment. Stimulation parameter interface 104 may include inputs to allow a user to select whether stimulation will be provided using biphasic (FIG. 2A) or monophasic pulses, and to select whether passive charge recovery will be used, although again these details aren't shown for simplicity.

Stimulation parameter interface 104 may further allow a user to select the active electrodes—i.e., the electrodes that will receive the prescribed pulses. Selection of the active electrodes can occur in conjunction with a leads interface 102, which can include an image 103 of the one or more leads that have been implanted in the patient. Although not shown, the leads interface 102 can include a selection to access a library of relevant images 103 of the types of leads that may be implanted in different patients.

In the example shown in FIG. 7, the leads interface 102 shows an image 103 of a single split-ring lead 33 like that described earlier with respect to FIG. 1B. The leads interface 102 can include a cursor 101 that the user can move (e.g., using a mouse connected to the clinician programmer 70) to select an illustrated electrode 16 (e.g., E1-E8, or the case electrode Ec). Once an electrode has been selected, the stimulation parameter interface 104 can be used to designate the selected electrode as an anode that will source current to the tissue, or as a cathode that will sink current from the tissue. Further, the stimulation parameter interface 104 allows the amount of the total anodic or cathodic current +I or −I that each selected electrode will receive to be specified in terms of a percentage, X. For example, in FIG. 7, the case electrode 12 Ec is specified to receive X=100% of the current I as an anodic current +I. The corresponding cathodic current −I is split between electrodes E2 (0.18*−I), E4 (0.52*−I), E5 (0.08*−I), and E7 (0.22*−I). Thus, two or more electrodes can be chosen to act as anodes or cathodes at a given time using MICC (as described above), allowing the electric field in the tissue to be shaped. The currents so specified at the selected electrodes can be those provided during a first pulse phase (if biphasic pulses are used), or during an only pulse phase (if monophasic pulses are used).

GUI 100 can further include a visualization interface 106 that can allow a user to view an indication of the effects of stimulation, such as electric field image 112 formed on the one or more leads given the selected stimulation parameters. The electric field image 112 is formed by field modelling in the clinician programmer 70. Only one lead is shown in the visualization interface 106 for simplicity, although again a given patient might be implanted with more than one lead. Visualization interface 106 provides an image 111 of the lead(s) which may be three-dimensional.

The visualization interface 106 preferably, but not necessarily, further includes tissue imaging information 114 taken from the patient, represented as three different tissue structures 114a, 114b and 114c in FIG. 7 for the patient in question, which tissue structures may comprise different areas of the brain for example. Such tissue imaging information may comprise a Magnetic Resonance Image (MM), a Computed Tomography (CT) image or other type of image and is preferably taken prior to implantation of the lead(s) in the patient. Often, one or more images, such as an MRI, CT, and/or a brain atlas are scaled and combined in a single image model. As one skilled in the art will understand, the location of the lead(s) can be precisely referenced to the tissue structures 114i because the lead(s) are implanted using a stereotactic frame (not shown). This allows the clinician programmer 70 on which GUI 100 is rendered to overlay the lead image 111 and the electric field image 112 with the tissue imaging information in the visualization interface 106 so that the position of the electric field 112 relative to the various tissue structures 114i can be visualized. The image of the patient's tissue may also be taken after implantation of the lead(s), or tissue imaging information may comprise a generic image pulled from a library which is not specific to the patient in question.

The various images shown in the visualization interface 106 (i.e., the lead image 111, the electric field image 112, and the tissue structures 114i) can be three-dimensional in nature, and hence may be rendered in the visualization interface 106 in a manner to allow such three-dimensionality to be better appreciated by the user, such as by shading or coloring the images, etc. Additionally, a view adjustment interface 107 may allow the user to move or rotate the images, using cursor 101 for example.

GUI 100 can further include a cross-section interface 108 to allow the various images to be seen in a two-dimensional cross section. Specifically, cross-section interface 108 shows a particular cross section 109 taken perpendicularly to the lead image 111 and through split-ring electrodes E2, E3, and E4. This cross section 109 can also be shown in the visualization interface 106, and the view adjustment interface 107 can include controls to allow the user to specify the plane of the cross section 109 (e.g., in XY, XZ, or YZ planes) and to move its location in the image. Once the location and orientation of the cross section 109 is defined, the cross-section interface 108 can show additional details. For example, the electric field image 112 can show equipotential lines allowing the user to get a sense of the strength and reach of the electric field at different locations. Although GUI 100 includes stimulation definition (102, 104) and imaging (108, 106) in a single screen of the GUI, these aspects can also be separated as part of the GUI 100 and made accessible through various menu selections, etc.

It has been observed that DBS stimulation in certain positions in the brain can evoke neural responses, i.e., electrical activity from neural elements, which may be measured. Such evoked neural responses are referred to herein generally as evoked potentials (EPs). One example of such neural responses are resonant neural responses, referred to herein as evoked resonant neural responses (ERNAs). See, e.g., Sinclair, et al., "Subthalamic Nucleus Deep Brain Stimulation Evokes Resonant Neural Activity," Ann. Neurol. 83(5), 1027-31, 2018. The ERNA responses typically have an oscillation frequency of about 200 to about 500 Hz. Stimulation of the STN, and particularly of the dorsal subregion of the STN, has been observed to evoke strong ERNA responses, whereas stimulation of the posterior subthalamic area (PSA) does not evoke such responses. Thus, ERNA may provide a biomarker for electrode location, which can indicate acceptable or optimal lead placement and/or stimulation field placement for achieving the desired therapeutic response. An example of an ERNA in isolation is illustrated in FIG. 8. The ERNA comprises a number of positive peaks ($P_n$) and negative peaks ($N_n$), which may have characteristic amplitudes, separations, or latencies. Notice that in the illustrated ERNA the first positive peak P1 is obscured within a stimulation artifact. The ERNA signal may decay according to a characteristic decay function. Such characteristics of the ERNA response may provide indications of the brain activity associated with the neural response.

FIG. 9 illustrates an example of how recorded neural responses, such as ERNA, can be used as surgical support to inform to inform electrode lead placement. An electrode lead 15 is advanced through the patient's neural tissue 902. As the lead is advanced, stimulation is provided at one or more of the electrodes; in this case stimulation is provided at the electrode E1. Neural responses are recorded at one or more of the electrodes; in this case, neural responses are recorded at the electrode E2. According to some embodiments, the stimulation that is provided may be stimulation that is configured for the purpose of evoking and recording ERNA responses. For example, the stimulation may comprise a burst of pulses followed by a quiescent period, during which the neural response may be recorded. A series of ERNA response signals 904 may be recorded as a function of the lead's depth with respect to the neural target. Notice that the amplitudes of the ERNA responses are greater when the recording electrode is near the target neural element. One or more waveform features of the ERNA response may be used to quantify the amplitude of the ERNA response signal. For example, the amplitude of one or more of the peaks (P1, P2, etc.) or an amplitude difference (P2−N1, etc.) may be used. According to some embodiments, the lead position resulting in the greatest ERNA amplitude may be considered the optimal lead placement. In other embodiments, other ERNA derivatives or features may be used in order to determine an optimal lead placement.

Figure 10:
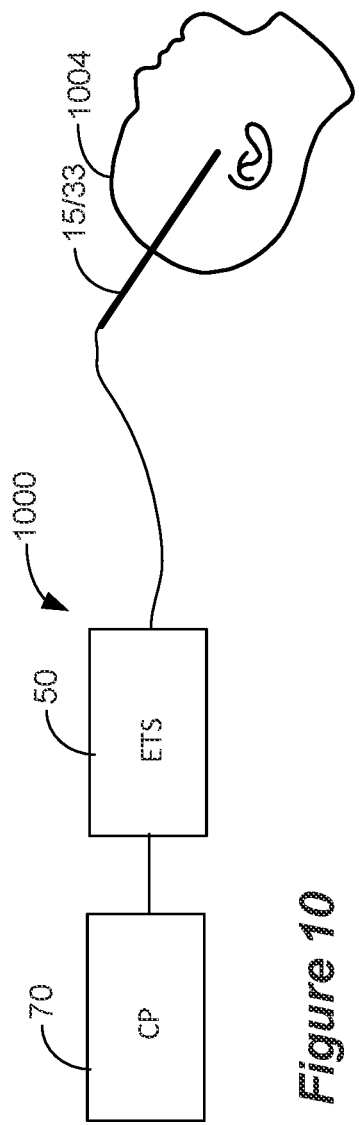
FIG. 10 illustrates an embodiment of a system for using recorded neural response signals for surgical support during electrode lead implantation.

FIG. 10 illustrates a schematic of a system 1000 for performing implantation of an electrode lead (e.g., lead 15 or lead 33, FIGS. 1A/1B) in the brain of a patient 1004, as described above (FIG. 9). The system 1000 also comprises one or more devices for controlling the stimulation and sensing provided at the electrode lead. The illustrated embodiment comprises a clinician programmer (CP) 70 for programming the stimulation and sensing parameters. The functionality of a CP 70 may be like that described above (FIG. 5), for example. The CP used during lead implantation may be the same machine or a different machine as the one used to program the patient's IPG later, during the fitting procedure. The clinician can use the CP 70 to select the electrodes of the lead 15/33 that will be used to provide stimulation, the parameters of the stimulation waveform(s) that will be applied, and the electrode(s) that will be used to sense evoked responses. In the illustrated system 1000, the CP 70 provides those selections to an ETS 50. The ETS 50 causes the stimulation to be applied to at leads. The ETS 50 also receives, and records sensed signals from the lead. The CP and ETS may communicate via a wired or a wireless connection. In the illustrated embodiment, a single ETS component is shown. However, according to some embodiments, multiple components could be used, for example, separate components for providing stimulation and for receiving and recording sensed signals. The CP may communicate with either or both ETS components in such an embodiment. According to some embodiments, aspects of the CP functionality and the ETS functionality may be combined in a single device. For example, the ETS 50 may itself be configured for programming the stimulation and/or sensing parameters. Alternatively, the functionality of receiving and recording the sensed signals (correlated with the stimulation configuration/parameters) may be embodied in the CP 70, for example as a module or subroutine additional to the CP functionality described above. Regardless of the exact configuration, the system is capable of causing stimulation of a defined waveform to be applied using selected one or more electrode on the lead, and of sensing/recording responses evoked by the stimulation. Further, the system 1000 (e.g., in either the CP 70 and/or the ETS 50) may comprise control circuitry configured to execute algorithms to suggest repositioning the lead based on the recorded ERNA signals.

It should be noted methodologies similar to that illustrated in FIG. 9 may also be used with a stationary lead implanted in an area of the patient's brain near a target neural element to determine which electrode(s) on the lead are nearest to the neural source of the ERNA. Rather than advancing the lead and recording ERNA responses as a function of depth, ERNA responses can be recorded at each of the electrodes of a stationary lead to determine which electrodes record the highest amplitude ERNA responses. Stated differently, the amplitudes of the ERNA responses recorded at the various electrodes may be used to determine the location of the ERNA source with respect to the electrode lead. Moreover, ERNAs recorded using electrodes (such as electrodes E2-E4 of lead 33 (FIG. 1B)) may be used to determine the rotational position of the ERNA source with respect to the electrode lead.

Additionally, recorded neural responses, such as the ERNA responses described above, may be used as biomarkers for informing the programming of various stimulation parameters, such as which electrodes (and/or current fractionalization among the electrodes) of the lead to use to deliver stimulation, stimulation amplitude, pulse width, frequency, patterns, and the like. For example, to determine the optimum stimulation location upon the lead, stimulation may be applied at various of the electrodes and ERNA responses recorded at one or more electrodes. The stimulation may be swept along the longitudinal and angular (i.e., rotational) positions on the lead one or more times to determine which stimulation location(s) provides the optimum ERNA response. For example, for the longitudinal sweep the electrode contacts at each longitudinal position can iteratively be used as the stimulating electrode and one or more of the same or other electrode contacts can be used as sensing/recording electrodes. According to some embodiments, directional electrodes at a given longitudinal location on the lead can be ganged together to act as a single ring electrode for stimulating and/or sensing during this step. MICC and current fractionalization can be used to provide stimulation at longitudinal "virtual electrode" locations between the electrodes. As each electrode contact from the proximal to the distal end of the lead is iteratively used as the stimulating electrode, evoked potentials are recorded at one or more of the other electrodes. This iterative process is used to create a comprehensive profile of the sensed evoked potentials relative to the locations upon the electrode lead both along and around the lead. This iterative stimulation location optimization process may be performed manually or automatically using optimization algorithms. Once the optimum longitudinal stimulation location is determined, the sweeping process may be repeated to optimize the rotational stimulating location by iteratively using different directional electrodes (and/or fractionalized angular locations) to provide stimulation and using the other electrodes as sensing/recording electrodes to record evoked potentials. Again, ERNA responses may be recorded at one or more electrodes and the rotational position that yields the optimal values for the neural responses may be selected as the rotational location for providing directional stimulation. As described above, MICC and current fractionalization may be used to determine optimum stimulation locations that are located between physical locations of actual electrode contacts. Again, the rotational optimization may be performed using optimization algorithms or may be performed manually.

Figure 11:
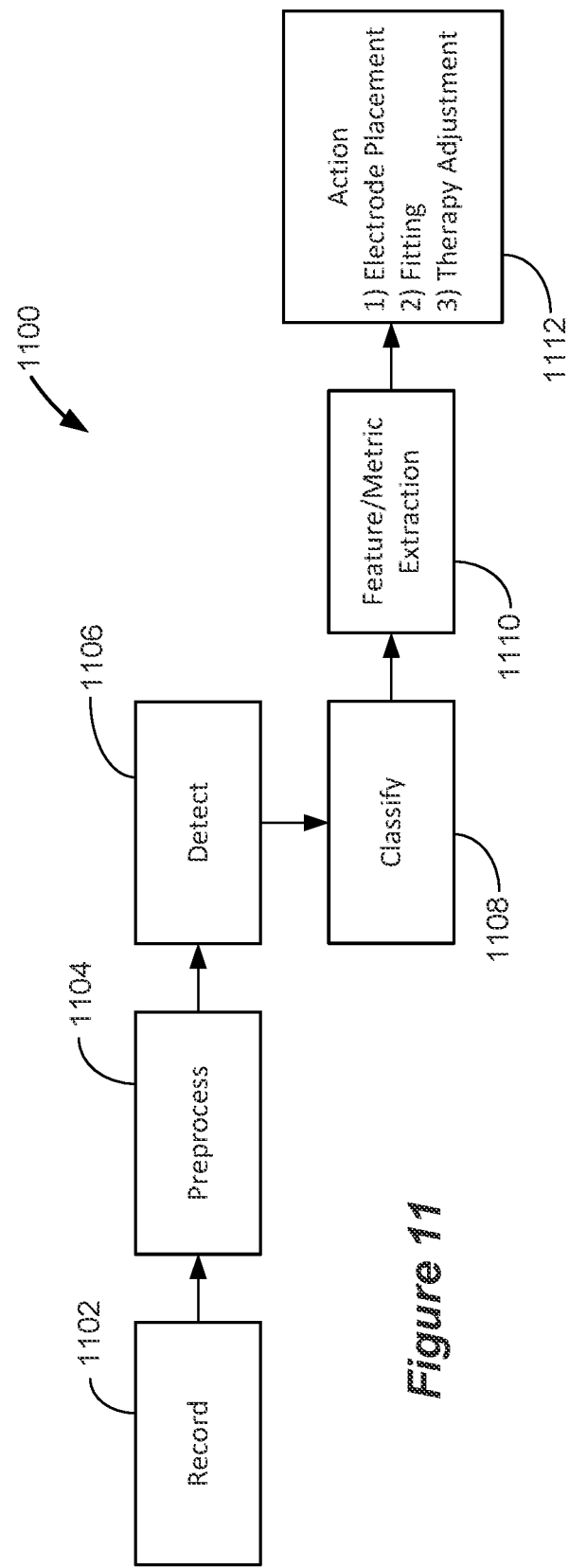
FIG. 11 illustrates an embodiment of a workflow for using recorded neural response signals to inform aspects of DBS.

FIG. 11 illustrates a generalized workflow 1100 for using sensed neural responses, such as ERNA, for informing aspects of neuromodulation therapy, such as DBS therapy. For example, the workflow may be used to provide surgical support to direct lead placement during the implantation of the electrode(s) for providing DBS therapy, as described above. The workflow 1100 may also be used following implantation surgery to facilitate the fitting procedure to program the patient's IPG for providing optimum therapy. The workflow 1100 may also be used during the patient's ongoing therapy to periodically adjust stimulation parameters using the recorded neural response (or waveform features of the neural responses) as a feedback/control variable. For example, the IPG may be programmed with one or more closed-loop feedback algorithms, such as Kalman filtering algorithms, heuristic algorithms, single or multiple threshold models, proportional-integral-derivative (PID) controller models, and the like. The control algorithm(s) may be used to control one or more stimulation parameters, such as current amplitude, frequency, pulse width, stimulation fractionalization, duty cycle, and the like, based on the features/metrics extracted from classified neural signals during ongoing therapy.

According to the workflow 1100, electrical activity (i.e., field potentials and the like) occurring at implanted electrodes may be recorded 1102 using one or more electrodes of the lead. Such recorded electrical activity may include evoked and/or innate neural activity, as well as other activity, such as stimulation artifacts. According to some embodiments, the recorded electrical activity may comprise ERNA responses, as described above. The recorded signal(s) may be preprocessed 1104 to reduce noise, eliminate stimulation artifacts, and the like. Peaks (or other waveform features) of the recorded signal or derivatives thereof may be detected 1106 to determine if a signal of interest is present. The detected peaks or other features may be classified 1108 to determine if they possess the right temporal or frequency characteristics (or other characteristics) to potentially serve as biomarkers and/or control signals that may be useful for informing aspects of therapy. Techniques for preprocessing, detecting, and classifying evoked neural responses of interest are described in U.S. Patent Application Publication 2022/0266022, the entire contents of which are incorporated herein by reference. If a given peak/feature does meet the criteria for serving as a biomarker and/or control signal, the peak/feature may be analyzed to extract certain features or metrics 1110. Such features or metrics can serve as feedback to inform various actions 1112 related to neuromodulation therapy. For example, changes in the feature/metric may be tracked or the value of the feature/metric can be compared to threshold values to determine whether to take some action regarding the therapy. Stated differently, the determined features/metrics may be indicative of the therapeutic efficacy of the stimulation, which may be tied to aspects of stimulation, such as lead placement, stimulation placement, electrode configuration, stimulation parameters, and the like. For example, U.S. Patent Application Publication 2022/0040486, the entire contents of which are incorporated herein by reference, describes using evoked responses for determining whether to move a stimulation lead or to adjust stimulation parameters. U.S. Patent Application Publication 2022/0296892, the entire contents of which are incorporated herein by reference, describes using evoked responses for determining and diagnosing a decline in a patient's stimulation therapy and also for optimizing stimulation parameters and/or stimulation location.

Generally, any value or metric may be used as the extracted waveform feature(s). Examples of such waveform features of the evoked potentials include but are not limited to:

- a height (amplitude) of any peak (e.g., P1 or N1);
- a peak-to-peak height between any two peaks (such as from N1 to P2);
- a ratio of peak heights (e.g., N1/P2);
- a peak width of any peak (e.g., the full-width half-maximum of N1);
- an area or energy under any peak;
- a total area or energy comprising the area or energy under positive peaks with the area or energy under negative peaks subtracted or added;
- a length of any portion of the curve of the evoked potential (e.g., the length of the curve from P1 to N2);
- any time defining the duration of at least a portion of the evoked potential (e.g., the time from P1 to N2);
- latencies of any peaks (P1 ... Pn, N1 ... Nn, etc.) as well as other feature-to-feature latencies;
- amplitude decay function;
- a time delay from stimulation to issuance of the evoked potential, which is indicative of the neural conduction speed of the evoked potential, which can be different in different types of neural tissues;
- a conduction speed (i.e., conduction velocity) of the evoked potential, which can be determined by sensing the evoked potential as it moves past different sensing electrodes;
- a rate of variation of any of the previous features, i.e., how such features change over time;
- a power (or energy) determined in a specified frequency band (e.g., delta, alpha, beta, gamma, etc.) determined in a specified time window (for example, a time window that overlaps the neural response, the stimulation artifact, etc.);
- spectral characteristics in the frequency domain (e.g., Fourier transform);
- a cross-correlation or cross-coherence of the evoked potential shape with a target optimal shape; and
- any mathematical combination or function of these features.

When using sensed neural responses, such as ERNA, as a biomarker to inform aspects of neuromodulation therapy, for example, as described with reference to FIG. 11, it may occur that some of the recorded neural response data of the recorded neural response signal becomes corrupted, is missing, obscured, distorted, contains artifacts, or is otherwise unavailable, unusable, or not fit for a particular purpose. As used herein, all such problematic data is referred to "corrupted." Additionally, data may become corrupted at various stages of evoking, recording, processing, transmitting, etc., and thus detection and classification may also occur at various stages. Certain data corruptions may be detected and partially addressed in analogue recording circuitry, digital recording circuitry, or circuitry inside the IPG or ETS designed to extract features from signals. Special data values or metadata may be used to note these data-corruptions for use downstream. Interpolation techniques described herein, therefor, may include detection and classification as part of the end-algorithms, or may operate on specially notated data (e.g. Not A Number, INF, Out Of Range) when performing interpolation. In some cases, when processing from signal to features, certain corruptions can cause corresponding features to be unavailable, which can be marked as missing data. In this way, portions of signals of features may be marked for later interpolation. For example, the patient may be fitted with a pacemaker that issues a pacing pulse during a time that the neural response signal is being recorded and the pacing pulse may interfere with the recording. Or in an operating room setting (for example, during lead implantation), a piece of operating room equipment might apply a potential during a measurement, which may corrupt the neural response data. For various reasons, the recording signal may include some type of artifact and/or "glitch" that corrupts a portion of the data. When using directional leads (such as lead 33, FIG. 1B), it has been found that bubbles may occlude one or more of the electrode segments (such as electrode E3), which may result in recorded neural response signals at the occluded electrodes being corrupted. As another example, sometimes an important feature of the neural response signal may be obscured by an artifact in the signal, such as a stimulation artifact.

Aspects of this disclosure relate to methods and systems for detecting when a corrupted signal is present, and/or identifying and selecting the corrupted channel(s) or time period(s), interpolating, extrapolating, and/or infilling recorded neural response data that is corrupted, missing, or otherwise unavailable. Note that in this disclosure, the term "interpolating" will be used broadly to include the usual meaning of the term interpolating, as well as extrapolating, infilling, and any method of calculating missing or corrupted data based on uncorrupted data and prior information. Also note that in this disclosure, the term "corrupted" will be used to refer to signals (or portions of signals) that are missing, obscured, or otherwise not usable or ideal.

Figure 12:
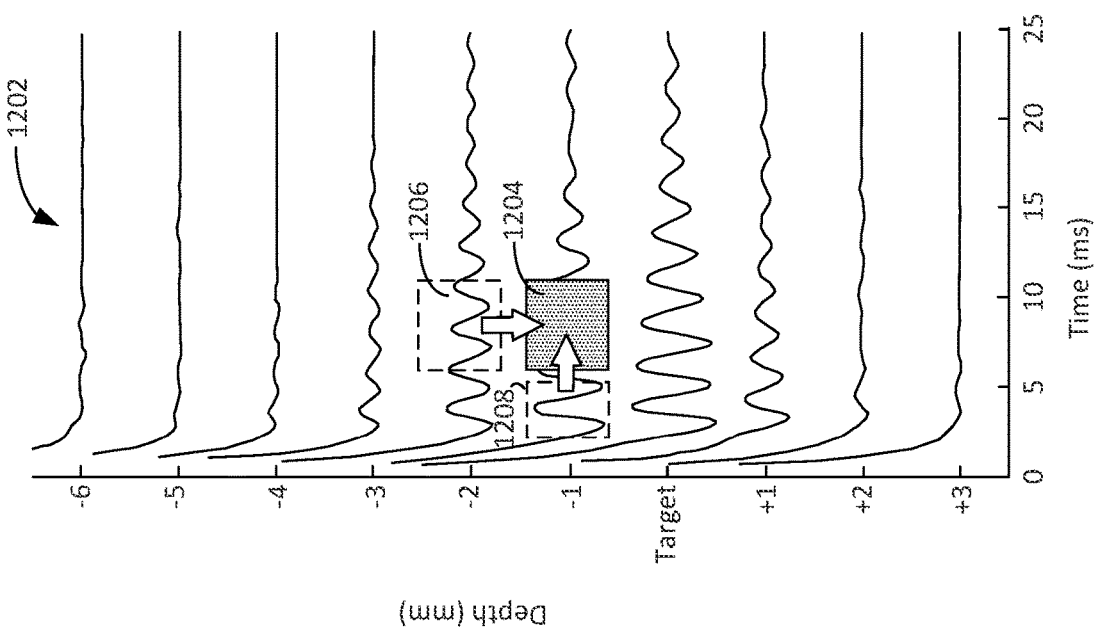
FIG. 12 illustrates a series of neural response signals wherein one of the neural response signals is corrupted.

For example, FIG. 12 illustrates a series of neural response signals 1202, similar to the one illustrated in FIG. 9, except that in the series 1202 part of the neural response signal data has been corrupted. Notice that a portion 1204 of the signal corresponding to the −1 mm measurement is missing. Aspects of this disclosure provide methods and systems for recovering or estimating that missing data. According to some embodiments, the missing data can be interpolated using portions 1206 of other recorded neural responses or other channels in the series. According to some embodiments, the missing data can be estimated based on data 1208 of the same channel, for example, earlier data (as shown) or later data. According to some embodiments, combinations of data from different channels and the same channel as the missing data may be used.

Figure 13:
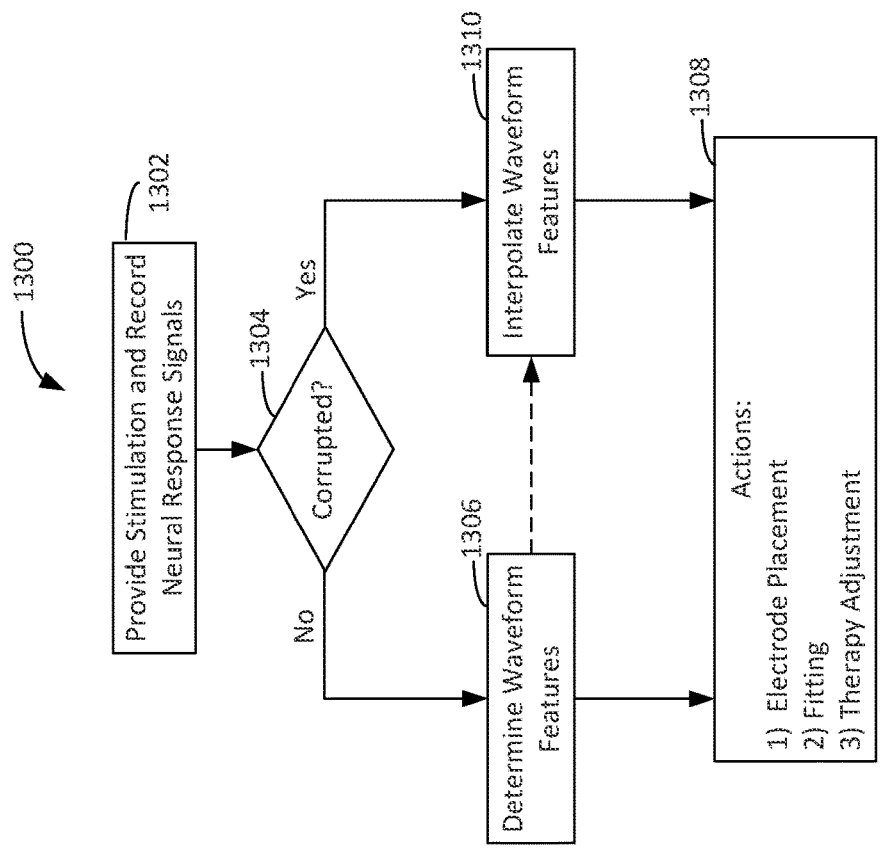
FIG. 13 illustrates an embodiment of an algorithm for using recorded neural response signals to inform aspects of DBS, wherein the algorithm includes interpolating waveform features for recorded neural response signals that are corrupted.

FIG. 13 illustrates one embodiment of an algorithm 1300 according to this disclosure. At step 1302, stimulation is provided using one or more electrodes implanted in the patient's brain and neural response signals are recorded at one or more electrodes. Generally, the neural response signals will be time-varying signals. According to some embodiments a series of neural response signals are recorded. For example, the neural response signals may be recorded at different depths as an electrode lead is advanced through a patient's neural tissue, yielding a series of recorded neural response signals as a function of depth (such as series 904 of FIG. 9 and series 1202 of FIG. 12). Alternatively, the series of neural responses may be recorded at multiple axially-spaced electrodes configured on a multi-electrode lead, such as electrodes 16 of lead 15 (FIG. 1A). Alternatively, the series of neural responses may be recorded at multiple circumferentially-space electrodes, such as directional electrodes E2-E7 of lead 33 (FIG. 1B). Still alternatively, the series of neural responses may be recorded at any combination of depths, directions, and/or electrodes. In addition, multiple trajectories may be recorded from by the same lead, and multiple leads may be recorded from in the same patient's brain. It should be noted here that, while the methods and systems described herein are primarily explained in the context of analyzing signals relating to neural responses that are evoked in the patient's brain by electrical stimulation, the methods and systems may also be used with respect to neural activity that is not evoked, i.e., to spontaneous neural activity.

At step 1304 the neural response signals are checked (i.e., classified) to determine if at least some of the data within the neural response measurements is missing, corrupted, or otherwise unavailable or undesirable. Processing the recorded neural response signals to determine if they are corrupted may be executed by hardware, firmware, and/or software. According to some embodiments, the algorithm may simply monitor the recorded data to determine if the signal or a portion of the signal is missing, for example, due to dropped packets. According to some embodiments, the algorithm may determine one or more features of the recorded signal, such as amplitude, slew rate, rise time, sharpness, etc., and determine if the feature is within an expected range, for example, above/below a threshold value, or between two threshold values. For example, the algorithm may determine if the recorded signal contains a comprises one or more peaks or troughs with a prominence exceeding a predetermined threshold value or values. The threshold values/ranges may be predetermined or may be dynamically set based on a population of recordings. If the features of the signal are outside of the expected range then the signal may be flagged as being corrupted, in whole or at least in part.

According to some embodiments, the algorithm 1300 may monitor the neural response signal to determine if the signal corresponds to expected neural response data. If the signal does not correspond to expected neural response data, then the algorithm may flag the signal as corrupted. For example, the algorithm may determine if the recorded signal comprises a number of peaks meeting or exceeding a predetermined threshold number of peaks within a predetermined time window. According to other embodiments, the algorithm may compare and attempt to match the recorded signal (or portions of the recorded signal) to one or more templates indicative of expected neural responses, such as ERNA responses as described above. Such templates may be stored and accessed in one or more template libraries or lookup tables or the like. The expected or template neural response may be based on prior measurements, which may be recent measurements from the same patient or may be measurements from other patients or groups of patients. The expectation of a particular neural response may be based on modeling, accumulated information about a "quintessential response," etc. Any methods of template matching may be used, such as cross correlation, sum of differences, neural networks, deep learning, machine learning, and the like. According to some embodiments, the recorded signal may be converted to the frequency domain, for example, using a Fourier transform (FT) or fast Fourier transform (FFT). The frequency domain data may be analyzed to determine if it corresponds to expected neural response data. For example, the data may be analyzed to determine if it has oscillation frequency characteristics/components corresponding to those of known neural responses, such as ERNA. According to some embodiments the algorithm may determine if one or more relative band powers in one or more predetermined frequency ranges of the frequency domain signal meet or exceed one or more predetermined thresholds. According to some embodiments, characteristics of the recording channels, such as impedance, may be monitored for indications that a given channel may have a problem and that data recorded on the channel might be corrupted.

Signals that are determined not to be corrupted can be processed to extract values for one or more waveform features from the signal (Step 1306). The extracted waveform features may be any of the waveform features described above, such as peak amplitudes, peak-to-peak amplitudes, etc. As explained above with reference to FIG. 11, and as explained in the incorporated applications, the extracted waveform features may be used as biomarkers to inform aspects of the patient's therapy. For example, as illustrated at Step 1308, the values of the waveform features may be used to inform actions, such as guiding placement of the electrode lead in the patient's brain during implantation surgery, fitting/optimization of stimulation parameters during the fitting process, and/or adjusting chronic therapy, for example using closed-loop feedback.

According to some embodiments, signals that are determined to be corrupted may be analyzed to determine what kind of 'corruption' is present. For example, the signal may be analyzed to determine if it is missing data, contains too much noise, contains a stimulation artifact, contains bleed from neighboring channels, etc. Signals that are determined to be corrupted may be analyzed to interpolate values for the waveform features (Step 1310). According to some embodiments, the values of the waveform features of the corrupted signals may be interpolated, at least in part, using the values of the waveform features determined from the uncorrupted signals. According to some embodiments, the values of the waveform features determined for the uncorrupted signals are fit to a curve (i.e., a mathematical function) that can then be used to interpolate the value of the waveform feature for the corrupted signal. Examples of curves that can be used to fit the waveform feature values include Gaussian distributions, skewed Gaussian distributions, Gaussians with an offset, spline functions, and the like. According to some embodiments, the mathematical function expresses the value of the waveform feature as a function of position within the brain (for example, depth and/or location of the recording electrode(s)).

FIG. 14 shows the series of neural response signals 904 from FIG. 9. Recall that the neural response signals 904 correspond to neural responses recorded as a function of depth as an electrode lead is advanced through a patient's neural tissue toward a target neural element. As mentioned above, notice that the amplitude of the neural response increases as the recording and stimulating electrodes approach the neural target. FIG. 14 also shows a curve 1102, which represents the amplitude of the first peak (P1) of each of the neural response signals plotted as a function of depth. In the illustrated example, the amplitude data is fit to a Gaussian distribution. In the case that the neural response signals for one of the depths were corrupted, the curve 1102 could be used to interpolate the value for the P1 amplitude at that depth. For example, assume that the neural response signal at a depth of −1 mm were to be corrupted, as illustrated in FIG. 12. In that case, the P1 amplitude corresponding to a depth of −1 mm could be estimated using value of the curve corresponding to −1 mm.

Figure 15:
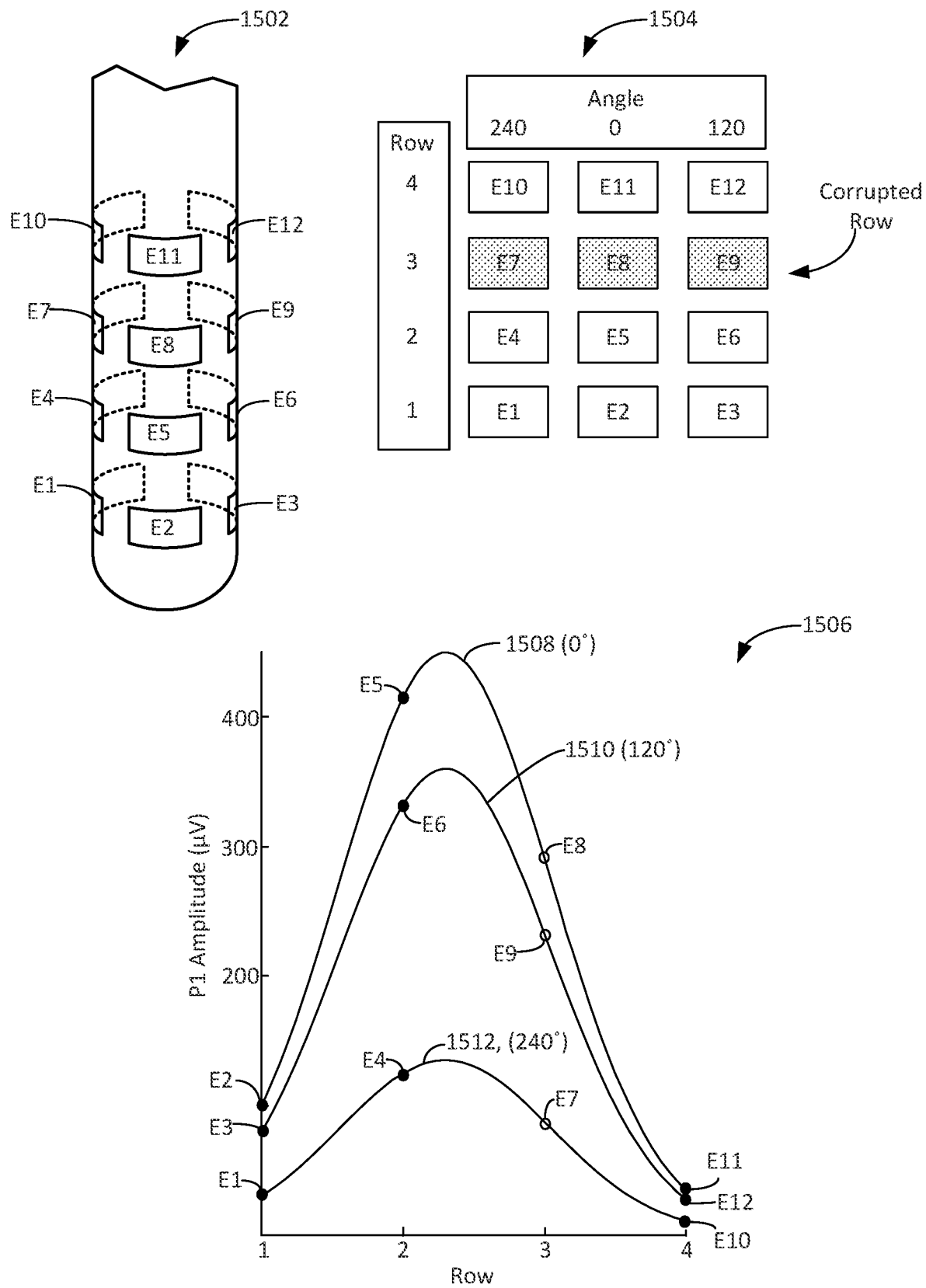
FIG. 15 illustrates interpolating missing or corrupted signals recorded using directional leads.

The methods and systems disclosed herein can also be used to interpolate neural response data from signals recorded using directional electrodes, wherein the signals from one or more of the directional electrodes have become corrupted or otherwise unusable. For example, FIG. 15 illustrates a directional lead 1502 having four rows of directional electrodes. Each row has three directional electrodes spaced at 120 degree increments around the central axis of the lead. The directional electrodes are labeled E1-E12. FIG. 15 also illustrates a two-dimensional representation 1504 of the lead, as might be represented on the GUI. The rows of electrodes are numbered from 1-4, distal to proximal. In the two-dimensional display, the center column of electrodes (E2, E5, E8, and E11) is chosen as 0 degrees, electrodes E3, E6, E9, and E12 are denoted as 120 degrees, and electrodes E1, E4, E7, and E10 are denoted as 240 degrees. In this example, assume that neural response signals are being recorded at each of the directional electrodes E1-E12. For each of the angles (i.e., 0, 120, and 240 degrees), one or more waveform feature values extracted from the neural response signals can be plotted as a function of row and a curves can be fit to the plots. For example, FIG. 15 shows a graph 1506 of P1 amplitudes extracted from each of the neural response signals. Line 1508 is a plot of each of the P1 amplitudes of the neural response signals recorded at the 0 degree electrodes as a function of row; line 1510 corresponds to the 120 degree electrodes; and line 1512 corresponds to the 240 degree electrodes. For each of the angles (i.e. directions) the recorded P1 amplitudes are fit to a Gaussian function. The functions for each of the directions can then be used to interpolate the extracted waveform feature value should the neural response signals at any of the electrodes be corrupted. For example, referring to the graph 1506, assume that neural response signals at each of the directional electrodes of row 3 are corrupted (i.e., electrodes E7, E8 and E9, illustrated as open circles to indicate that the values are missing). The Gaussian functions for each of the directions can be used to interpolate the P1 amplitudes for the corrupted neural response signals. For example, the function fit to plot 1508 can be used to calculate the P1 amplitude value for E8; plot 1510 can be used to for E9; and plot 1512 can be used for E7. As mentioned above, other functions may be used instead of Gaussian functions, depending on the particular embodiment. In some cases, the information available may only be sufficient to reconstruct some, but not all, features of the corrupted data. In the cases of directional leads, it may be that only 'ring mode' information, containing no directionality, can be reconstructed. In other cases, only one of multiple missing directional channels can be reconstructed, or the reconstructions can have different levels of certainty or confidence, which can be associated with the data for later use, display, or sharing.

Figure 16:
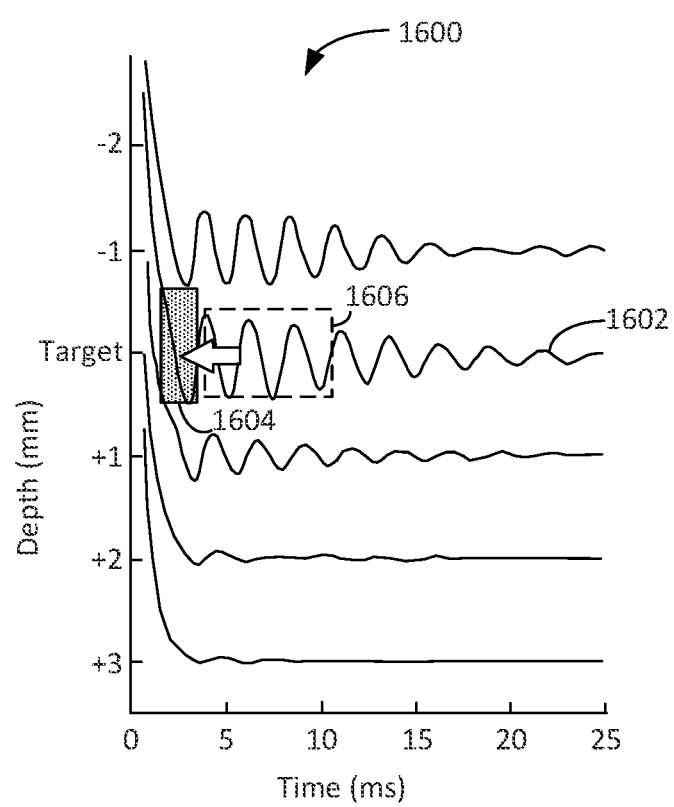
FIG. 16 illustrates a series of recorded neural response signals wherein a portion of one of the neural response signals is corrupted and uncorrupted data of the corrupted signal is used for interpolation to recover the corrupted part.

According to some embodiments, data on a channel may be corrupted only for a period of time. For example, a neural response signal may be corrupted by a stimulation artifact immediately following stimulation. FIG. 16 illustrates a series 1600 of neural response signals recorded as a function of depth, as has been described above. Notice that on the signal 1602 corresponding to the target depth, the time interval 1604 where one would expect to observe the P1 peak is obscured by stimulation artifact. Assume that the P1 amplitude is the waveform feature we would like to use as a biomarker, as described above. However, since that region of the neural response signal is corrupted (i.e., obscured by the stimulation artifact), the P1 amplitude is not available by direct extraction. According to some embodiments, the P1 amplitude may be interpolated based on waveform signals for other depths, optionally combined with the information from the target depth, as described above. According to other embodiments, the corrupted data may be interpolated based on uncorrupted portions 1606 of the neural response signal 1602 itself. In other words, the corrupted portion of the neural response signal can be interpolated using uncorrupted portions of that same signal. In some embodiments, this may be performed by fitting a model to the known portions of 1602 and projecting or extrapolating into the corrupted portion 1604. In other embodiments, the distribution of the e.g. P1 peaks across the depths may be modeled, and the target channel projected by interpolation. Information from previous recordings can also be used, e.g. by template matching, to determine a projection. In still other cases, previous recordings at the same depths, but having used a different recording parameter, e.g. amplitude, may be available, and the missing data can be projected by fitting the different recordings and scaling the missing data from the available recording.

It will be apparent to a person of skill in the art that methods and systems for interpolating waveform features for corrupted recorded neural response signals have been described herein. Instructions for configuring control circuitry of one or more devices for carrying out the disclosed methods may be stored on a non-transitory computer readable media, such as on a magnetic or optical disk, in solid state memory, etc. Depending on the particular implementation, the instructions may be executed using one or more of the devices described above, thereby configuring the device (specifically, the control circuitry of the device) for and causing the device to perform the disclosed methods. For example, in embodiments wherein the waveform features are used for as biomarkers for surgical support, for example, to inform and/or guide electrode implantation, the methods may be performed using CP 70 and/or ETS 50, as illustrated and discussed in reference to FIG. 10. In embodiments wherein the waveform features are used to guide fitting and optimization of stimulation parameters, the methods may be performed using CP 70 and/or IPG 100, as discussed in reference to FIGS. 5 and 7, for example. In embodiments wherein the waveform features are used for feedback control of stimulation parameters, for example, during ongoing chronic therapy, the methods may be performed by the IPG 100, as discussed with reference to FIG. 6.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of monitoring neural activity in a patient's brain and using the neural activity to configure electrical stimulation for treating Parkinson's Disease (PD), using one or more electrode leads in the patient's brain, wherein each electrode lead comprises a plurality of electrodes, each of which may be configured for stimulating or recording, the method comprising:
    using two or more of the electrodes as recording electrodes to record a plurality of signals each indicative of neural activity in the patient's brain, wherein each of the plurality of signals is recorded on a different recording electrode,
    for each recording electrode, determining if the signal recorded at that electrode is corrupted by converting the signal from a time domain signal to a frequency domain signal and determining if the frequency domain signal comprises one or more frequency components corresponding to frequency components characteristic of a known neural response,
    determining values for one or more waveform features for each of the plurality of signals recorded at recording electrodes that do not comprise corrupted signals,
    interpolating values for one or more waveform features for each of the corrupted signals, wherein the interpolating comprises using the waveform feature values determined for the non-corrupted signals recorded at recording electrodes that do not comprise corrupted signals,
    using the interpolated values to configure therapeutic stimulation for treating PD, and
    administering the therapeutic stimulation to the patient.

2. The method of claim 1, further comprising providing electrical stimulation to the patient's brain using one or more of the electrodes, and wherein the neural activity is evoked by the electrical stimulation.

3. The method of claim 1, wherein the plurality of signals are each time-varying signals.

4. The method of claim 1, wherein determining if the signal is corrupted comprises determining if one or more waveform feature values derived from the signal are outside a predetermined range.

5. The method of claim 1, wherein determining if the signal is corrupted comprises matching the signal with one or more template signals or portions, wherein the template signal corresponds to a prior or an expected neural response.

6. The method of claim 5, wherein the expected neural response comprises an evoked resonant neural response (ERNA).

7. The method of claim 1, wherein the interpolating comprises fitting the values for the one or more waveform features for each of the plurality of signals that is not corrupted to a model and using the model to interpolate the values for the one or more waveform features for each of the corrupted signals.

8. The method of claim 7, wherein the model is a Gaussian function or a spline function.

9. The method of claim 7, wherein the model expresses the value of the one or more waveform features as a function of spatial position and/or orientation within the brain.

10. The method of claim 1, wherein the one or more waveform features are selected from the group consisting of amplitudes of any peaks, peak-to-peak height between any two peaks, a ratio of heights of any two peaks, and an area under any one or more peaks.

11. An external medical device configured to monitor neural activity evoked by electrical stimulation in a patient's brain and use the neural activity to configure electrical stimulation for treating Parkinson's Disease (PD), wherein the electrical stimulation is provided by one or more electrode leads configurable to be placed in the patient's brain, wherein each electrode lead comprises a plurality of electrodes, each of which may be configured for stimulating or recording, the external medical device comprising:
    control circuitry configured to:
        cause a first one or more of the electrodes to provide stimulation to the patient's brain,
        use a second two or more of the electrodes as recording electrodes to record a plurality of signals each indicative of neural activity evoked in the patient's brain, wherein each of the plurality of signals is recorded on a different recording electrode,
        for each recording electrode, determine if the signal recorded at that electrode is corrupted by converting the signal from a time domain signal to a frequency domain signal and determining if the frequency domain signal comprises one or more frequency components corresponding to frequency components characteristic of a known neural response,
        determine values for one or more waveform features for each of the plurality of signals recorded at recording electrodes that do not comprise corrupted signals, and
        interpolate values for one or more waveform features for each of the corrupted signals, wherein the interpolating comprises using the waveform feature values determined for the non-corrupted signals recorded at recording electrodes that do not comprise corrupted signals,
        use the interpolated values to configure therapeutic stimulation for treating PD, and
        administer the therapeutic stimulation to the patient.

12. The device of claim 11, wherein determining if the signal is corrupted comprises determining if one or more waveform feature values derived from the signal are outside a predetermined range.

13. The device of claim 11, wherein determining if the signal or portion is corrupted comprises matching the signal with one or more template signals, wherein the template signal corresponds to a prior or an expected neural response.

14. The device of claim 13, wherein the expected neural response comprises an evoked resonant neural response (ERNA).

15. The device of claim 11, wherein the interpolating comprises fitting the values for the one or more waveform features for each of the plurality of signals that is not corrupted to a model and using the model to interpolate the values for the one or more waveform features for each of the corrupted signals.

16. The device of claim 15, wherein the model is a Gaussian function or a spline function.

\* \* \* \* \*